(12) United States Patent
Baley, Jr. et al.

(10) Patent No.: US 11,337,388 B2
(45) Date of Patent: May 24, 2022

(54) MAIZE PLANTS WITH IMPROVED DISEASE RESISTANCE

(71) Applicant: MONSANTO TECHNOLOGY LLC, St. Louis, MO (US)

(72) Inventors: George J. Baley, Jr., St. Louis, MO (US); Romain Jean-Baptiste Fouquet, Amendeuix-Oneix (FR); Sonali Dilip Gandhi, Bangalore (IN); Prashant Ganpatrao Golegaonkar, Bangalore (IN); Hongwu Jia, Apex, NC (US); Yule Pan, Chesterfield, MO (US); Jeffrey Michael Stein, Wildwood, MO (US); Dharanendra Swamy, Bangalore (IN); Hao Zhou, Iowa City, IA (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 15/586,140

(22) Filed: May 3, 2017

(65) Prior Publication Data

US 2018/0116140 A1    May 3, 2018

Related U.S. Application Data

(60) Provisional application No. 62/331,918, filed on May 4, 2016.

(51) Int. Cl.
| | | |
|---|---|---|
| *A01H 1/00* | (2006.01) | |
| *A01H 1/04* | (2006.01) | |
| *C12Q 1/6895* | (2018.01) | |
| *A01H 1/02* | (2006.01) | |

(52) U.S. Cl.
CPC ............. *A01H 1/1255* (2021.01); *A01H 1/02* (2013.01); *A01H 1/04* (2013.01); *A01H 1/045* (2021.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,273,944 B2 * | 9/2012 | Kerns | C12Q 1/6895 800/265 |
| 8,536,424 B2 | 9/2013 | Trifunovic et al. | |
| 8,569,598 B2 | 10/2013 | Trifunovic et al. | |
| 8,664,490 B2 | 3/2014 | Page | |
| 8,692,059 B2 | 4/2014 | Brinkman et al. | |
| 8,697,942 B2 * | 4/2014 | Tomas | A01H 1/04 800/267 |
| 8,710,321 B2 | 4/2014 | Trifunovic et al. | |
| 8,710,329 B2 | 4/2014 | Faue et al. | |
| 8,802,946 B2 | 8/2014 | Page | |
| 9,210,869 B2 | 12/2015 | Frederickson et al. | |
| 9,220,216 B2 | 12/2015 | Lynch et al. | |
| 9,226,471 B2 | 1/2016 | Lynch et al. | |
| 9,629,317 B2 | 4/2017 | Zhao et al. | |
| 2015/0026839 A1 | 1/2015 | Baley et al. | |

FOREIGN PATENT DOCUMENTS

| | | |
|---|---|---|
| WO | WO 2008/143993 | 11/2008 |
| WO | 2009029771 A2 | 3/2009 |

OTHER PUBLICATIONS

Maize GDB gpm674c, https://www.maizegdb.org/data_center/locus/955342, accessed Jun. 8, 2018.*
Maize GDB TIDP5534, https://www.maizegdb.org/data_center/locus/201247, accessed Jun. 8, 2018.*
Maize GDB TIDP5534 (https://www.maizegdb.org/data_center/locus/1201247, accessed Nov. 20, 2020).*
Maize GDB Gpm674c (https://www.maizegdb.org/data_center/locus/955342, accessed Nov. 20, 2020).*
Maize GDB umc21 (https://www.maizegdb.org/gene_center/gene/41444, accessed Nov. 20, 2020).*
Maize GDB bnl3.03 (https://www.maizegdb.org/data_center/locus/40645, accessed Dec. 21, 2020).*
Lee et al., "Expanding the genetic map of maize with the intermated B73×Mo17 *(IBM) population,"* Plant Mol Biol, 48:453-461, 2002.
Andorf et al., "MaizeGDB update: new tools, data and interface for the maize model organism database," *Nucleic Acids Res*, 44:D1195-D1201, 2015.
Invitation to Pay Additional Fees regarding International Application No. PCT/US2017/030579, dated Jul. 31, 2017.
International Search Report and Written Opinion regarding International Application No. PCT/US2017/030579, dated Sep. 9, 2017.
Afolabi et al., "Novel Sources of Resistance to Fusarium Stalk Rot of Maize in Tropical Africa," Plant Disease 92(5):772-780, 2008.
Gai et al., "Infection cycle of maize stalk rot and ear rot caused by Fusarium verticillioides," PLos One 13(7):e0201588, 2018.
Extended European Search Report regarding Europe Application No. 17793128.4, dated Sep. 13, 2019.
Pe et al., "Mapping Quantitative Trait Loci (QTLS) for Resistance to Gibberella Zeae Infection in Maize," Molecular and General Genetics 241 (1/02):11-16, 1993.

(Continued)

*Primary Examiner* — Anne Kubelik

(74) *Attorney, Agent, or Firm* — Dentons US LLP; Matthew Madsen

(57) ABSTRACT

The present invention is in the field of plant breeding and disease resistance. More specifically, the invention includes a method for breeding corn plants containing one or more markers that are associated with resistance to fungi. The invention further includes germplasm and the use of germplasm containing at least one marker associated with resistance to *Fusarium* stalk rot (FSR) infection for introgression into elite germplasm in a breeding program, thus producing novel FSR resistant germplasm.

18 Claims, No Drawings

Specification includes a Sequence Listing.

(56) References Cited

OTHER PUBLICATIONS

Yang et al., "Genetic analysis and molecular mapping of maize (*Zea may* L.) stalk rot resistant gene Rfgl.", Theoretical and Applied Genetics 108(4):706-711, 2004.
Ding et al., "QTL Mapping of resistance to Fusarium ear rot using a RIL population in maize," Molecular Breeding 22(3):395-403, 2008.
Zhang et al., "Fine Mapping of QTL for resistance to stalk rot in maize," Theoretical and Applied Genetics 123(3):585-596, 2011.

\* cited by examiner

SEQUENCE LISTING

<160> NUMBER OF SEQ ID NOS: 230

<210> SEQ ID NO 1
<211> LENGTH: 1129
<212> TYPE: DNA
<213> ORGANISM: Zea mays
<220> FEATURE:
<221> NAME/KEY: misc_feature
<222> LOCATION: (351)..(351)
<223> OTHER INFORMATION: n is a, c, g, or t

<400> SEQUENCE: 1

```
gttttgttga gagatacaaa aatttgagtt ccttcaacga aactgaggta gtgttccaaa      60
taaaagcttt atcttcgctg atcagcatag aatatgttgg ttttctgtta atcgaaagtc     120 gaaaccata acttctttg ctggttttct tatagctcgc gaatctgcat aaggaattga     180
ggcctcatat tctacggcgg gttataaaag atgttgagaa gtctttacct cctaaaatcg     240
agaggattct acgtgttgag atgtcaccc tccagaaaca gtgagtactc cgggctaatt     300
ttcttgaacc aatcttttt gacaagtttt cttattagtt tggatggaat nggaacccgc     360
attcttaaat cttttttcc aagctccaaa ccctccctgg accttggagc tgccaaacat     420
gcccttattg tacactgagg ctaatttttt ggtttttact aggtactaca agtggatttt     480
agagcggaat tttcagaatc tgaataaagg tgttcgtggg aatcaggttt tcgttacatc     540
ttgttcttct aatcaagttc ttatgtttta tattttccgt gcctttagtt atttcagttg     600
gcacatcttg gaattgaatg caatttggct gtctcagtat gtagcaaatt gaaccttatg     660
tctcagtatg tatatatacc gttgctgcta gtctaagacc attttcttg ctaaatgctg     720 tggtgcttgc caggatcttg attggaacaa tgttactatt ctttctcacc tactattgct     780
aggtcaagca gttcctcacc tgctattgct agctcaagaa gtttctcacc tggccgtgca     840
ttacctatca aactggagca tgggcaaggc cacaaggcaa gacttggctg ttgtgagcca     900
aatctgctct cccatgtggg caatgattga ttgtttataa cttcatgtct gatctactaa     960
attcaaataa ttagtgtgct tggtaacaat tgttcttaag gcacatccaa atctgccctc    1020
caaaaaatta gtgtcctgct atcatgtttt atgtgactga cttgttaatg acatgcaggt    1080
atcacttctt aacattgttg ttgaattgaa gaaatgctgc aaccatcca              1129
```

<210> SEQ ID NO 2
<211> LENGTH: 751
<212> TYPE: DNA
<213> ORGANISM: Zea mays
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(8)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (566)..(567)
<223> OTHER INFORMATION: n is a, c, g, or t
<220> FEATURE:
<221> NAME/KEY: misc_feature
<222> LOCATION: (588)..(594)
<223> OTHER INFORMATION: n is a, c, g, or t
<220> FEATURE:
<221> NAME/KEY: misc_feature
<222> LOCATION: (598)..(599)
<223> OTHER INFORMATION: n is a, c, g, or t
<220> FEATURE:
<221> NAME/KEY: misc_feature
<222> LOCATION: (611)..(613)
<223> OTHER INFORMATION: n is a, c, g, or t
<220> FEATURE:
<221> NAME/KEY: misc_feature
<222> LOCATION: (616)..(617)
<223> OTHER INFORMATION: n is a, c, g, or t
<220> FEATURE:
<221> NAME/KEY: misc_feature
<222> LOCATION: (619)..(622)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (647)..(654)
<223> OTHER INFORMATION: n is a, c, g, or t
<220> FEATURE:
<221> NAME/KEY: misc_feature
<222> LOCATION: (657)..(666)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (686)..(715)
<223> OTHER INFORMATION: n is a, c, g, or t
<220> FEATURE:
<221> NAME/KEY: misc_feature
<222> LOCATION: (717)..(750)
<223> OTHER INFORMATION: n is a, c, g, or t

<400> SEQUENCE: 2
ccncnnnnct aagctgnagt ctcactatcc tatatactaa agtgacatgg ctgcaagcga    60
atgccatcca gttctgccat tagcaaaata agttatgcgt aaaaactttg cttcatatgt   120 acattttct atgttttgtt gattgttatc actattcaaa gggttgaagt gtacacacct    180
agtaaatggt tagccctaca tgaatattgt cctgcgattt acttattgtg gcttccttct   240
tatagagcca tgtatgaaac ttgttaccct gcaaatngaa cctgttgcaa agtgtcttaa   300
gtttagaggt gtgatgtaat gttattacca atctgcanaa aatgttaccc caattcagaa   360

```
attggctcta tcatcctttt gtttatcatc gtgcttaact gtgttgcttt ttgcccataa    420
gaagacaagt tattgttgct attgttcttc tgtaccacac caatagcata atccaatgtt    480
ttgaagatgt tgtgccttt gaagtacaac aaatcatgta aatgtttggg ctttggagtc     540
tttcatgatt tgtttgtttc ttgcannctg catgtgatga aacttctnnn nnnncagnnc    600
aagcatttct nnnacnncnn nnaagttcga cnaatgggga caacatnnnn nnnntgnnnn    660
nnnnnnacta catatgatga tnantnnnnn nnnnnnnnnn nnnnnnnnnn nnnnngnnnn    720
nnnnnnnnnn nnnnnnnnnn nnnnnnnnnn a                                   751
```

```
<210> SEQ ID NO 3
<211> LENGTH: 649
<212> TYPE: DNA
<213> ORGANISM: Zea mays
<220> FEATURE:
<221> NAME/KEY: misc_feature
<222> LOCATION: (341)..(341)
<223> OTHER INFORMATION: n is a, c, g, or t

<400> SEQUENCE: 3
```

```
gccaatgaaa gatcacccct tagcagtaag aacattctgt tgcaaactaa tgcttatatt    60
agccatcagt ttatcagcct tttactactt tgcatgtagt tggagtgttc gaaatctgat    120
gctcaagggc agcttggcag aactttggag gatgcacaga acataactga attatcaaat    180
caggagaacc tgttacccac ggtgtctcct ggctttatat caacgtctaa tgggaaaggt    240
atgaacttca gaaactctac ccatggtcaa aatgggcata gtttgctaca taactgaggc    300
atacatgaaa gtagaagatt gatgattgga tttctgtgtg naggtactaa catacatgat    360
actcaatttg aggaagagcc gacaggtatg aacaacagcc ttattgaacc taatggaaat    420
gatgacatgt gcacagacca tgctgctacc aaattagcta aaagcaacca tgttatggaa    480
acagctaccc tacctattga tgggagttca cagtgcatca ttgacatttc tccattgagg    540
agctgctctg ctttggagag atctttgcct tcaccaccgc aggcttcgtt cgtcaagagg    600
tcacctgtgt ggcatgtagt tgacgcaaaa catgtgttta aggagttac                649
```

```
<210> SEQ ID NO 4
<211> LENGTH: 610
<212> TYPE: DNA
<213> ORGANISM: Zea mays
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (592)..(597)
<223> OTHER INFORMATION: n is a, c, g, or t

<400> SEQUENCE: 4
```

```
ggctcctgac atgaaggtga agtcgtcttc cgctgttttnt gtacgtgcac tcgactaatt      60
cggccgattc agggttgcat cgctcacgca tggactaaaa cgccagggaa tgaatctaat     120
attgtaagaa cgatgggatt gaatagcgca cgnctcgcac acatgtcagt cgttcatgtg     180
acagagcttg cttgtacacn tccattgacg tgcaagttat tatcgtcatg aagaggcgct     240
ggtcccatgt taagttccgg cacgtgatcc gcgcacggcc agccctgctg cacctgacct     300
ggcctgttga gtaattaagt catcatcgnt cacgtagagt gctcaagtaa aatactcctc     360
cctctgccct tcgnagccac aaattctaag cgacgcgaat cgcagccaca caccaccagc     420
agcaccaaga gccagatcag atcagcctga tgaactcact gccaccactc aaggcgcgcg     480
ggccgtacca atgagcatcg tctgcccgag tagagtatac aagtattata agccggcgag     540
agcataacgt cgcgtataaa ttaatattca tcgtacgatg ccttgcgcga cnnnnnntgc     600
tacccacgcg                                                             610
```

```
<210> SEQ ID NO 5
<211> LENGTH: 657
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (595)..(627)
<223> OTHER INFORMATION: n is a, c, g, or t
<220> FEATURE:
<221> NAME/KEY: misc_feature
<222> LOCATION: (629)..(651)
<223> OTHER INFORMATION: n is a, c, g, or t

<400> SEQUENCE: 5
```

```
ncngcattcn ntgcgaaaaa nnnngggtgg aaggtgagat attttggtat ttgtttctat      60
cagaaagtaa catattttat agagccaaac ttccttttg cggtatcttc tgcttgggat     120
cactctctct tatttgagat attactttgt tgtagcctna tacttttgt aatgtggcaa     180 tatttcagga cgtagaggca acaatacatt gtgcagaatg gctttcaatg gttggaggaa     240
```

| | |
|---|---|
| ctagcaccgg tgaccaaaga attaggtaaa caatnagatg cttaccaagt tttctagtta | 300 |
| attatgtagt ttctgcaccc tgcgcttttt ctttaatctt ctaggcatgt agtttttgtg | 360 |
| gtttatcggt tatcatgttt ttttngttc ccccaagagt gcacatgtat ttttccctta | 420 |
| gatcaaattc aagctgatag ctttttttctt gatttcata ttcctattct gttaagaagt | 480 |
| atgtaatgac ataccaggt tggtgatatc ttgtgctatt ttgttctttt taaggcgtga | 540 |
| agaagcatta ccaattttca agaggagatt actgggtagt ctgctnaatt tttcnnnnnn | 600 |
| nnnnnnnnnn nnnnnnnnnn nnnnnnntnn nnnnnnnnnn nnnnnnnnnn ntacatg | 657 |

<210> SEQ ID NO 6
<211> LENGTH: 370
<212> TYPE: DNA
<213> ORGANISM: Zea mays
<220> FEATURE:
<221> NAME/KEY: misc_feature
<222> LOCATION: (323)..(323)
<223> OTHER INFORMATION: n is a, c, g, or t

<400> SEQUENCE: 6

| | |
|---|---|
| agcgtgtcct ctcgaccagc caaccatggc gcccacagat ggagacagaa accagatccg | 60 |
| tcgaaagaga tgcttggccg ccgtgccgat actgtgcatt aattctgaca agacaagggc | 120 |
| cgcccgtcta aattgtctcc ctaactttct gatcggacgg cggggagagc caaacaaaca | 180 |
| gggaaatggc acatgcgact ccatgccatg gccatagcag taagcagcaa tttgcatcgg | 240 |
| acagcgagtt gcagccgacc acgccaaggt gaaggacggg tcactctggt caccagaggg | 300 |
| gccaactgca cccagatctg ctngtccacg cctctcgaca cttgtccgag ttattctacg | 360 |
| gctggataaa | 370 |

<210> SEQ ID NO 7
<211> LENGTH: 1294
<212> TYPE: DNA
<213> ORGANISM: Zea mays
<220> FEATURE:
<221> NAME/KEY: misc_feature
<222> LOCATION: (121)..(145)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t

<400> SEQUENCE: 7

| | |
|---|---|
| caaaacaagg tttcagtaaa ctggctctta aaccttggcc cttcactggg cattgtccgc | 60 |
| gttcgaggca ttgggctaat acatacagaa ctaatgtctg gaatcccagc tatcttctcc | 120 |
| nnnnnnnnnn nnnnnnnnnn nnnntccac caggtactgg tattcctatg tgtcaaatca | 180 |
| gttcctgtgc cacatgtgca accggaggaa cgatttctgg tgggtcgcat tggtccaaaa | 240 |
| gagtataggc tatacagggt cattgtcaga tatggttatc gcgatgtgca aaggatgac | 300 |
| ctggagttcg agaaggagct agtcagcaac attgcagagt tcatccgcag cagtggggaa | 360 |
| tatgacaaga atggcttcgt ggaggacaca gataagccct tgcccttcga gaagctgtcc | 420 |
| accatcagta ccggaatcaa tatgttggaa gaggatggag aagttgatgc atatgtatcc | 480 |
| cctcataagg agatagaccc acacaatgca gcacccaagc gaaagaaagc caggttcatg | 540 |
| ataccaaaga gtgctcaggt ggacagtgag gtgcgccgcg agctgcagga gctcatggac | 600 |
| gctagggagg caggcatgtc cttcatcctg gggcactcgt acatgaaggc gaagagcggg | 660 |
| tcgagtttca taaagcggat tgtgataaac ttcttctacg agttcttgag gaagaacagc | 720 |

```
cgtggccctg catacgccgc aaacataccc catgcctcca ctctggaggt aggaatggtc      780
taccaggtct gacaacagtt agcagctgtg taaaggtaga gagagatgag acgacgcctg      840
tcagcgccac ctgtatatat ccacttgttg ctgccgatac cgttaacaca atcacaggat      900
gacacgagta gtgagtgncc cttgagcaca gccaatgctg aggaagcagc tgaagatgag      960
atcatctgtg gagagcccag ccagaagtat gcattttttg tttgtagagc cttttgttgt     1020
gccggtagtt gttaagtttc gtatgttgc tgctgttgtt tagtttcgta cttgtgagct      1080
gtaattgtct gtaagagtga ctagcaaaat actgtagcat ttttgacgtt cagcagcggc     1140
ctctgtagtt ctgtcacttg tctataattg aggactgtat aggtagcagc taaacattct     1200
agtaggggct gatgtcgttg ggccgcctgt attatagact gggccgtaaa gcacagcttc     1260
tttcgggcct aagaacgtct ggaagacaaa ccac                                 1294

<210> SEQ ID NO 8
<211> LENGTH: 397
<212> TYPE: DNA
<213> ORGANISM: Zea mays
<220> FEATURE:
<221> NAME/KEY: misc_feature
<222> LOCATION: (262)..(262)
<223> OTHER INFORMATION: n is a, c, g, or t

<400> SEQUENCE: 8
ctagagattg atctctggtc gcttggatgc attttggcag aactgatgaa actggaggct       60
ttgttcccgg ggatatctga tattgatcag attagtagaa tcatcaatgt cctgggcgat      120
ataacagaag aaacctttcc aggctgttca aacttgccag attacaacaa gatttccttt      180
aacaaagttg agaaaccgac aggccttgaa gcatgtctgc taacagatc tcctactgag       240 gttagcatca taaagcagct antttgctat gacacagcaa agaggaccag tgctgttgat      300
ctgctgaatg atcggtactt taccgaagag ccattgccgg cacctataga aggattacat      360
gtcccggcat caaaggacga ggatgatgac agctcaa                              397

<210> SEQ ID NO 9
<211> LENGTH: 367
<212> TYPE: DNA
<213> ORGANISM: Zea mays
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (357)..(363)
<223> OTHER INFORMATION: n is a, c, g, or t

<400> SEQUENCE: 9
gagctgtatc tgtaagcagc tgcacagtag cagcagcatc acgaacccga tgatgcagtc       60
ggtcttgtac tgcatgttgc cggcgcaacg caagtacttc gctcaggctt cccacanga      120 tccaaacagg cgcagcttct ctgctacaac agctttcatt gcctctttag cagacgccat      180
cacctgaatc aagtcctttt ctggctttct gagggacgcc aggtagctgt tccgaacctc      240
ggtgttcaca ttgaattttc tcacgcccaa gtctatgcac tcctgctcca gaaattagtg      300
cactgttata gcgcctacac gataagtttt atcctaataa tacttgagat atggccnnnn      360 nnntagc                                                               367

<210> SEQ ID NO 10
```

<211> LENGTH: 385
<212> TYPE: DNA
<213> ORGANISM: Zea mays
<220> FEATURE:
<221> NAME/KEY: misc_feature
<222> LOCATION: (115)..(115)
<223> OTHER INFORMATION: n is a, c, g, or t

<400> SEQUENCE: 10

```
agctggcgtc tgtaagggaa gtacttaaaa agtcagaagg agaactcgag atcacctcga    60
agcagttagt tttggtttca gaagcacata gtgaccttaa taaagaattg ctggntgcat   120
ataagcagtt agagtccacg caaagtgagc tagtgaaaga gcgtaaaatc aatgctactc   180
ttaacatgga gcttgaggct ttggtgaaac aatcagtgat agagtccgaa gcaagaaaaa   240
ctcttcaagt cgacttggat gaggccacta gatcactaaa tgaggtgaat aagagtacac   300
tctgtctgtc taagcagctg gaaacaacta attccaagat ttctgctatt aaagaggaga   360
aagatatgct gtcaatgttc cttga                                         385
```

<210> SEQ ID NO 11
<211> LENGTH: 760
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (587)..(589)
<223> OTHER INFORMATION: n is a, c, g, or t
<220> FEATURE:
<221> NAME/KEY: misc_feature
<222> LOCATION: (614)..(620)
<223> OTHER INFORMATION: n is a, c, g, or t
<220> FEATURE:
<221> NAME/KEY: misc_feature
<222> LOCATION: (622)..(625)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (641)..(644)
<223> OTHER INFORMATION: n is a, c, g, or t
<220> FEATURE:
<221> NAME/KEY: misc_feature
<222> LOCATION: (648)..(650)
<223> OTHER INFORMATION: n is a, c, g, or t
<220> FEATURE:
<221> NAME/KEY: misc_feature

```
<222> LOCATION: (653)..(653)
<223> OTHER INFORMATION: n is a, c, g, or t
<220> FEATURE:
<221> NAME/KEY: misc_feature
<222> LOCATION: (655)..(659)
<223> OTHER INFORMATION: n is a, c, g, or t
<220> FEATURE:
<221> NAME/KEY: misc_feature
<222> LOCATION: (668)..(670)
<223> OTHER INFORMATION: n is a, c, g, or t
<220> FEATURE:
<221> NAME/KEY: misc_feature
<222> LOCATION: (672)..(673)
<223> OTHER INFORMATION: n is a, c, g, or t
<220> FEATURE:
<221> NAME/KEY: misc_feature
<222> LOCATION: (677)..(687)
<223> OTHER INFORMATION: n is a, c, g, or t
<220> FEATURE:
<221> NAME/KEY: misc_feature
<222> LOCATION: (690)..(691)
<223> OTHER INFORMATION: n is a, c, g, or t
<220> FEATURE:
<221> NAME/KEY: misc_feature
<222> LOCATION: (693)..(700)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (707)..(711)
<223> OTHER INFORMATION: n is a, c, g, or t
<220> FEATURE:
<221> NAME/KEY: misc_feature
<222> LOCATION: (716)..(726)
<223> OTHER INFORMATION: n is a, c, g, or t
<220> FEATURE:
<221> NAME/KEY: misc_feature
<222> LOCATION: (729)..(738)
<223> OTHER INFORMATION: n is a, c, g, or t
<220> FEATURE:
<221> NAME/KEY: misc_feature
<222> LOCATION: (740)..(758)
<223> OTHER INFORMATION: n is a, c, g, or t

<400> SEQUENCE: 11
ggccngactg ctcctgcgaa gacgangctg acatcgagta cgacagcagc cgtatctggg      60
ttctggacnc gcccaacata ccaaagcctc caccagagac ggagaggcta gtgattatgg     120
gcggtgacta caccagaatg gacacgtatt acgtcatgcc caatgggaag cgtgcgaggt     180
gtgctggtga cgtggacaag tttctggang caaatccagc gtacaaaagc cgcatatctg     240
cttcggattt cgactttgca ccgcccgagg ttgttgagga gactgttgtt tctcacaatt     300
ttctgcctct gcaaggttgc caaggccaag aaacaggaga aggcagagag gcacacaaaa     360
taggtgaaag cagagaggca tcgatgctct gaactgtgcc tgtgccctgt gctatgtagg     420
tgatagtccg ctcaagatca cgtcacgtct cgttcctatc tagtacggtt gtctatctcg     480
gctgaagtta atgtagtagg tcttcttgcg tgttaattcc tngggaatat atgagatgtt     540
taataattag ttgcttaggc cttaaaactg tgcttcctta acttttnnnc ttcagtcatc     600
tcgtatatgc acgnnnnnnn cnnnngctag cagcntagnc nnnnactnnn cancnnnnna     660
tcatagcnnn anntctnnnn nnnnnnngcn ngnnnnnnnn ctnacannnn ntacannnnn     720
nnnnnngann nnnnnnnnan nnnnnnnnnn nnnnnnnnat     760

<210> SEQ ID NO 12
<211> LENGTH: 397
<212> TYPE: DNA
```

```
<213> ORGANISM: Zea mays
<220> FEATURE:
<221> NAME/KEY: misc_feature
<222> LOCATION: (262)..(262)
<223> OTHER INFORMATION: n is a, c, g, or t

<400> SEQUENCE: 12
ctagagattg atctctggtc gcttggatgc attttggcag aactgatgaa actggaggct    60
ttgttcccgg ggatatctga tattgatcag attagtagaa tcatcaatgt cctgggcgat   120
ataacagaag aaacctttcc aggctgttca aacttgccag attacaacaa gatttccttt   180
aacaaagttg agaaaccgac aggccttgaa gcatgtctgc ctaacagatc tcctactgag   240
gttagcatca taaagcagct antttgctat gacacagcaa agaggaccag tgctgttgat   300
ctgctgaatg atcggtactt taccgaagag ccattgccgg cacctataga aggattacat   360
gtcccggcat caaaggacga ggatgatgac agctcaa                            397

<210> SEQ ID NO 13
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 13
tctttaaaaa aatgaccacc aatcattcaa gctagcaatg ccctggtcgt tgtgtgtgca    60
atgcgatgcg cacgagagaa gacgcacgca tcaagcgaga nggtcgcgca cgcgatcgag   120
accgttcatt agtgggagg gacgaccaag taaacaagac gtaccaggaa tgaggtgaag    180
agcgcgaaga aggcgccgaa g                                             201

<210> SEQ ID NO 14
<211> LENGTH: 544
<212> TYPE: DNA
<213> ORGANISM: Zea mays
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(10)
<223> OTHER INFORMATION: n is a, c, g, or t
<220> FEATURE:
<221> NAME/KEY: misc_feature
<222> LOCATION: (14)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
```

```
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (264)..(271)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (451)..(452)
<223> OTHER INFORMATION: n is a, c, g, or t
<220> FEATURE:
<221> NAME/KEY: misc_feature
<222> LOCATION: (455)..(457)
<223> OTHER INFORMATION: n is a, c, g, or t
<220> FEATURE:
<221> NAME/KEY: misc_feature
<222> LOCATION: (464)..(466)
<223> OTHER INFORMATION: n is a, c, g, or t
<220> FEATURE:
<221> NAME/KEY: misc_feature
<222> LOCATION: (468)..(470)
<223> OTHER INFORMATION: n is a, c, g, or t
<220> FEATURE:
<221> NAME/KEY: misc_feature
<222> LOCATION: (472)..(474)
<223> OTHER INFORMATION: n is a, c, g, or t
<220> FEATURE:
<221> NAME/KEY: misc_feature
<222> LOCATION: (476)..(477)
<223> OTHER INFORMATION: n is a, c, g, or t
<220> FEATURE:
<221> NAME/KEY: misc_feature
<222> LOCATION: (493)..(512)
<223> OTHER INFORMATION: n is a, c, g, or t
<220> FEATURE:
<221> NAME/KEY: misc_feature
<222> LOCATION: (514)..(518)
<223> OTHER INFORMATION: n is a, c, g, or t
<220> FEATURE:
<221> NAME/KEY: misc_feature
<222> LOCATION: (526)..(528)
<223> OTHER INFORMATION: n is a, c, g, or t
<220> FEATURE:
<221> NAME/KEY: misc_feature
<222> LOCATION: (534)..(538)
<223> OTHER INFORMATION: n is a, c, g, or t
<220> FEATURE:
<221> NAME/KEY: misc_feature
<222> LOCATION: (540)..(542)
<223> OTHER INFORMATION: n is a, c, g, or t

<400> SEQUENCE: 14
nnnnannnnn tctnnnnang tcttcgcnct cgtcgttgct gttttcatgt acattgtcgt    60
tcacatcttg ctgtccttcg anaaaatggc acgggtcatg aagaggactg gagaacagtg   120
ggttccatgt ctgaagaaga tgtgggcact cattgaaant gaacctccaa accatcagcc   180
atcttcagag gaaccatgag aggctgaccc ttgncngtat ncttgtattg tgattacatg   240
aattgttcaa ttgatatgta cctnnnnnnn ntagaatcaa tatttgtttt ccccacttgt   300
ttaaggttga agtgttgtaa tcttttttatg cacttanaga taagatgcat tcatccanga  360
```

```
gggttagctt caagtacttc gttcttggtt ttaactttct cagtatattg gacggccgga    420
actacttatt tgtagctacc tctagcagtc nntcnnntta ttcnnnannn annncnntct    480
aaagtgtata atnnnnnnnn nnnnnnnnnn nnannnnnat atacannntc tacnnnnnan    540 nncc                                                                  544
```

<210> SEQ ID NO 15
<211> LENGTH: 1343
<212> TYPE: DNA
<213> ORGANISM: Zea mays
<220> FEATURE:
<221> NAME/KEY: misc_feature
<222> LOCATION: (6)..(10)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(76)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (317)..(318)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1040)..(1040)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1282)..(1282)
<223> OTHER INFORMATION: n is a, c, g, or t
<220> FEATURE:
<221> NAME/KEY: misc_feature

```
<222> LOCATION: (1309)..(1311)
<223> OTHER INFORMATION: n is a, c, g, or t
<220> FEATURE:
<221> NAME/KEY: misc_feature
<222> LOCATION: (1320)..(1328)
<223> OTHER INFORMATION: n is a, c, g, or t

<400> SEQUENCE: 15
tctgtnnnnn ctatctctcc ttctccgtct ctttcttctg tgttcttcct ccattgctct      60
gtacttattn atnnnngcgc gctgccttt caancagggg caagatcctc gaggtgctca     120
agaactggcc cgagaggagc atccaggtca tcgtcgtcac cgacggcgag cgcatcctcg     180
gcctcggtga tctcggttgc cagggggatgg gaattcccgt tggcaagctc tccctctaca     240
ctgccctcgg aggtgttcgc ccgtcagctg taagtgctgc tcacaatgct cnttcttcag     300
tattactact nctgntnngn aataaacttg tagcactagt cgtagtagga aagatttgga     360
atcgattttt tttcttcagt attactacta cttcagtatt attngtcgta ataatgttta     420
cgctgctgca gtgcctgccc atcacaattg atgtcggcac caacaacgag gccttgctca     480
aggacgagtt ctacatcggc ctccgccaga ggcgtgccac cggcgaggtc agcaactcat     540
ctgcaatccc ctccattgat ttagttctac ccctacatgg ctgttctgtt cacccacttg     600
cagctggtga ttttgttnaa cctgtaacca gtctcttgtc tggattattg agacgtggct     660
tgtgttttg atggttcaca ggagtaccat gaacttcttg aagagttcat gaccgccgtc     720
aagcaaaact acggcgagaa ggtcctcacc caggtcagtc tcagtggacc agccacagat     780
actaccagct gttggttttc gccttttggg ccgaactttc tctcatcctg gatctgaaat     840
ggatgttctt tttgacctct gaccgtgcag ttcgaagact cgccaaccaa caacgccttt     900
gacctgctcg agaagtacag ggagagccat ctcgtcttca acgacgatat ccaggtaggc     960
taggctttcc ttgtgacagc gcatcacagg caaacagnag caccatggat gccaagttca    1020
gaacagggc ctgcctgttn tgtgctcgtt ccgtcgtccg tttctttcca ccgtgctgaa    1080
cgaaaacgat gcggatgtgt gtgattgctg cagggaacag cntccgtggt cctcgctggc    1140
ctcctggcgg cgctcaaggt ggtcggcggg acactngcgg accacactta cctgttcctc    1200
ggcgccggcg aggtcggtcg atttgacttg ctagtatact gcatcagtgt taccctatct    1260
tttctttgcc gatcaaagct tnggatcact cgcggcctca ttcttttcnn ngattacgtn    1320
nnnnnnnnca tctgcaggcc ggg                                             1343

<210> SEQ ID NO 16
<211> LENGTH: 201
<212> TYPE: DNA
<213> ORGANISM: Zea mays
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 16
tctctagaat cggatgcgcg canagcaaca acagtagagt catagcaggc aactcgttgg      60
caaagcccac cactccccc aaggcccaag cattagtgca ntacatcaag tatatgctgg     120
gcacgcagtc gcgggcagac tcagcagag attgtactgg gaaaatcata tatgaccaaa     180
taaatactag gaggcaagca c                                               201
```

<210> SEQ ID NO 17
<211> LENGTH: 493
<212> TYPE: DNA
<213> ORGANISM: Zea mays
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t

<400> SEQUENCE: 17

```
gatgaactttt gctgtgttta tcaatgcttg gaacttgtgt tctaatgtgt cagtgatccc      60
tggaactgac aaaagcagcc caaactcctg gtggatcgtg gataacctcg tcaaaanttg     120
catagatgag cagttggctg ataccaatca aattctgaca tctccaggaa gcaatattcc     180
acttctagcg tggatgntga cagagcccat ttcctggcac cttcttgtaa tccaatcctg     240
tatgagatct atggctccac aagggaagaa gaagaagaaa ggcgggccat ctgagcgacc     300
aaacacacct cacctgcagg caattcggag ctccgttcag tgcatgnctg acactctcca     360
gagagtccag aaatgtctgt cagaacagat gaagccagaa gagcaagctc tagacatgct     420
ggtgtcacat ttgcaaggaa ccggtgccga aggccctgga cagatcgccc gtatcttgga     480
cgagagcgca gca                                                        493
```

<210> SEQ ID NO 18
<211> LENGTH: 201
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 18

```
ctgnttttc atatctngac attgtgattt agtaagttgc tcatatattc tactacattc       60
tttagcacgc tttccncaag gggggcagtt ttaggcattc ntactgtggt tctgaatgaa     120
gagataaatg atactccctc attcctgaag tctctgaccg aatttataga aattagtacc     180
aacatttctc tctncaaata a                                               201
```

<210> SEQ ID NO 19
<211> LENGTH: 201
<212> TYPE: DNA
<213> ORGANISM: Zea mays

<220> FEATURE:
<221> NAME/KEY: misc_feature
<222> LOCATION: (101)..(101)
<223> OTHER INFORMATION: n is a, c, g, or t

<400> SEQUENCE: 19

```
atgccatcta gttgctcctt ctccacaagt ctgaaaaaca atgaacttat tcctatatga    60
attcttaata gaggtccttc tatatgacaa acagctctcc nttgtcgtag agggagggac   120
tgtagcatac ctgtattgaa gaactgcatg ttgcttgctg caggagggat gatctgtggg   180
gacatctgca actttccttt c                                            201
```

<210> SEQ ID NO 20
<211> LENGTH: 854
<212> TYPE: DNA
<213> ORGANISM: Zea mays
<220> FEATURE:
<221> NAME/KEY: misc_feature
<222> LOCATION: (5)..(12)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t

<400> SEQUENCE: 20

```
tgcannnnnn nngctgttaa tctcacatcc tgctctgtcc agaacccttc ctcagccatg    60
gcataactca aatcaagaat cttctcaaag agtgtcctct tgtttgacct ccactcattc   120
aggaacttga tcaaccgacc aacattcaca tgaagatcct tctcttctgc aaatgggtat   180
gcctgaatat agtccttcct gtaaatagta ggtggataga aagccacata tccaccaatc   240
tcccacaaga tccgttgcgc ccagtaccca cggatcacnt ctgctgccat tgagctcaca   300
gacactggca tcatnagccc ccagaaagca ggtgactgga acaatgtatt gaacgagttc   360
actggtgcca tcatgccctg aggtagtgcc accttcgggg cttccgaatc aaacctcaga   420
tcgaacgccg aagttggtgg ttttctagtg aagtagaaca ccgcatctac atctggcaac   480
ccgtccgaca gcccctgctg aatgaattgc cggccactga agacctcggt gtagaacacc   540
tcatgggcga cctccccaac cttatcgagc ggcagccccc ttggccagac cgaccgctgg   600
ccgaagtgca cgtaggggtt caccactgtg cgattgggat ccgcgtggct gtactggagc   660
agcactgggt ggttggtgac tccagatccc aaatccacgt cgaaatgctt ccccagatcg   720
ttcccgggca cctcggcgcg gtcgtcggcg tcgaagatca ccttggcccc gtgctggatg   780
gcgaagaggt agcccgccgt cttgcggacg tgggagccgt agggcaggaa gtcgacggag   840
cggtatccga gctg                                                    854
```

<210> SEQ ID NO 21
<211> LENGTH: 685
<212> TYPE: DNA
<213> ORGANISM: Zea mays
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t
<220> FEATURE:

<221> NAME/KEY: misc_feature
<222> LOCATION: (654)..(654)
<223> OTHER INFORMATION: n is a, c, g, or t

<400> SEQUENCE: 21

```
gagacagtat tatgttctta tcttttatga gagcttccag atcagtttcc ataaactcaa    60
atacaaggtg caaattttcc ttgtaaggga acaatcaat  cagctctata atattaggac   120
ctttcagctc cttaagtagt ttaatttccc tcaatgcggt gaagttaaca ccttccttct   180
tgtccttccc tacccagatt ctctttaccg cgactgtatt tccagtctga aaatgaacag   240
catccagcaa ctcatgaaca aaacaggtca atcagaatga aaaactacta ctccctccgt   300
tccaaattat aagttgtttt ggttttttcta gatacattgt tttaattaca tatccagtta  360
ttttttttaaa ccaaagaccc tacgtctgag tgcatagcaa aagatatgta tctaaaaaat  420
tatgtatcta gaaaagacaa aatcttataa tttggaatgt anagagtaca aaatatgaga   480
gaacattaag aacagtcgga aggctgaacc gtggtgattc tatcacagcc acgtatactt   540
gactgagaaa agtaaaaacg gtgatgacac cacttaagac cagtgagaac acatcccaca   600
tctgttgtca ctcttacacg cgtggaatac ataagtccac caaaaaaant caanccccggt  660
atccaacaga acacgagaac tacca                                         685
```

<210> SEQ ID NO 22
<211> LENGTH: 454
<212> TYPE: DNA
<213> ORGANISM: Zea mays
<220> FEATURE:
<221> NAME/KEY: misc_feature
<222> LOCATION: (27)..(27)
<223> OTHER INFORMATION: n is a, c, g, or t

<400> SEQUENCE: 22

```
cgcactcgta gtagcactaa aaaaaangtc aagtcagagg cggcgacacc ccgcgtcacg    60
tgccgtcggt gcggcaggaa cgataagcgc tcgtcgcgcc tagatctcac ccatacaaaa   120
ttcgtttgcg ccatgcagac gcgccacgcc aaccgtctct gccgagccgc cgtcgacttc   180
ctgcctcaga taaaataaaa ggttgatcct tgcgtgcgtg ccgctgatac gactcccgac   240
cgggtccatt tcggcggcac gccccgccgc gttccccacc gcgctatatt gcgtgccgct   300
gatacgagtc cacatcgcca tcgcgtccca cacgctcaca gtcacagcat ggcacgccac   360
cctctcgcgg ctgctgtcct cttcctctgc ctgctgtcgg tctgccgcgc ggccggcgcc   420
ggcgccggcg ccgctggcaa aggtaaaccg agca                               454
```

<210> SEQ ID NO 23
<211> LENGTH: 402
<212> TYPE: DNA
<213> ORGANISM: Zea mays
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (389)..(394)
<223> OTHER INFORMATION: n is a, c, g, or t

<400> SEQUENCE: 23

```
ttgaatttct ttgattccat ttcttgacag cataagcatc cacctgtgga tgtgtcctcc    60
aggagaaaac atgtgaaccc gccgagcatt catttcaaac ttcaaaatag gccatcatg    120
gagggagaga aacgttatga cgaagtanac aaatctgtcg ctgtcaccgt cttcattacc   180
```

| | |
|---|---|
| attgcctaaa gcaaaatcat cttctctgaa catcaattca gtcattgaag cccatgtgta | 240 |
| cctccatttc cttgacaaga gacatgttct tacagcttct tttattggca aacagcagag | 300 |
| aattttatct ttaataacat caggtagatt actgatgatg tcaacatttg taacagattt | 360 |
| atgtctttc ttttgagaac ctccacgann nnngggtat ac | 402 |

```
<210> SEQ ID NO 24
<211> LENGTH: 487
<212> TYPE: DNA
<213> ORGANISM: Zea mays
<220> FEATURE:
<221> NAME/KEY: misc_feature
<222> LOCATION: (204)..(204)
<223> OTHER INFORMATION: n is a, c, g, or t

<400> SEQUENCE: 24
```

| | |
|---|---|
| cacccggagc cgcgccccgc ggagcaccct gcgcccgttc ctcaacaagg accccgctc | 60 |
| gtcggcctcc tccgccacca gcacgcccgc caggcccgcc gcgcccgggc taccgccgga | 120 |
| gcggagcggg gtcctggaca gcagctcggg cgcggaggcg gcggggctcg tcgtcatcgc | 180 |
| ggactccgcg aagaggctcg ggantgacct cgtggagagg agccgagagg ccggcctacc | 240 |
| ggtgccgccc tcggtgacct tggctgtggg actgggacgc gaggcgggcg ctgcgggatc | 300 |
| gccgcgcccc gtcgcggccg cagctcttcc tgctgccgct tttttcagca ttgcgggcaa | 360 |
| gaaaccggag cccgagcctc tgatccgacc aacttcagcc gagcgcccga gcctgatcga | 420 |
| cccgatcgat ctacgcagag tagctagcta gaaacagcaa gatgtgtggg acgaaacggt | 480 |
| cagctca | 487 |

```
<210> SEQ ID NO 25
<211> LENGTH: 912
<212> TYPE: DNA
<213> ORGANISM: Zea mays
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (461)..(905)
<223> OTHER INFORMATION: n is a, c, g, or t

<400> SEQUENCE: 25
```

| | |
|---|---|
| ggcctccctg ctctcgcggt gccgccccga ctgcccggtc ttcgccttca cgacgtcgac | 60 |
| gtccgtcagg aggcggctga acctgcagtg gggcctgatc cccttccgcc tcgccttctc | 120 |
| cgacgacatg gagagcaacc tgaaccgcac cttctccctg ctcaaggcca ggggcatgat | 180 |
| ccagtccggg gacctcgtga tcgccctctc ggacatgctg cagtccatcc aggtgatgaa | 240 |
| cgtaccctga ggtagaagag ccttaccttt acctccatgc cgcatggtcc cgtatcggaa | 300 |
| ggaaggaaca cgcgcgttat cggcaccttg gaaggacggt tncttcttc cctgcgccta | 360 |
| aatcgctgcc ctttgttttc gctgtatcag atgctgctat gctatgctag gctctagtct | 420 |
| ggcccaggga actgtggcaa taatctgtgg ctttcaggct nnnnnnnnnn nnnnnnnnnn | 480 |
| nnnnnnnnnn nnnnnnnnnn nnnnnnnnnn nnnnnnnnnn nnnnnnnnnn nnnnnnnnnn | 540 |
| nnnnnnnnnn nnnnnnnnnn nnnnnnnnnn nnnnnnnnnn nnnnnnnnnn nnnnnnnnnn | 600 |
| nnnnnnnnnn nnnnnnnnnn nnnnnnnnnn nnnnnnnnnn nnnnnnnnnn nnnnnnnnnn | 660 |
| nnnnnnnnnn nnnnnnnnnn nnnnnnnnnn nnnnnnnnnn nnnnnnnnnn nnnnnnnnnn | 720 |

```
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnccccc cc                                                         912

<210> SEQ ID NO 26
<211> LENGTH: 785
<212> TYPE: DNA
<213> ORGANISM: Zea mays
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (775)..(778)
<223> OTHER INFORMATION: n is a, c, g, or t

<400> SEQUENCE: 26
ttgaacgttc cccagcgcct tntcgccgtc gtcgatgagt agcttctttc ggagggccag     60
cagctcctcc ccggcaccgc agatgtaggc cgacgttcgc ctgccggaga gagttgctcc    120
ttccatgctg tcnatgtagt cctgcatgta cagcacaaat aagaccaatg taccatgtcc    180
taccgatgtt tgcatgttgc aagataggag gaaaaaaaac attccaaggt gttcagacgc    240
catgaaattg aaatgaaatt gaatggttg tttctgatgg ttttctgagc cattggttaa    300
aacaaactca aggcattcag acattagttt tctgggcctg ttgatggctg tagctaggtc    360 gatgttttn atgtacaaca atacctgttt cgtgtaagat ccagagagga agaagttttt    420
aacgggcgtc ttctgatcag gcctgaatgg gtcgtttcca ggagcctcac ggtacagcga    480
ttgtccgatc tttaccacac tggaccatgt aacttccaag ccccgggaag atgggaacag    540
ttctacaacc tgtgggaaaa ttacatgtgt ttattactga ngtgagcttt ggaagaatac    600
aaaataacat aagcagaaga aatctctctn ttttnaagtg cattgaaatg gggtcttgct    660
cagntatgtg taaagggaac agcagaaatt tgancnaaac agaagctatt tacaaaccta    720
```

```
cctgcttttg aaccttacta atgatctcct cgtttggcaa tggcatgtat ggatnnnnag    780
gagtc                                                                785

<210> SEQ ID NO 27
<211> LENGTH: 1138
<212> TYPE: DNA
<213> ORGANISM: Zea mays
<220> FEATURE:
<221> NAME/KEY: misc_feature
<222> LOCATION: (456)..(456)
<223> OTHER INFORMATION: n is a, c, g, or t

<400> SEQUENCE: 27
ttatgaagca aaggggatg ccacattctg taaaagggat tattctcatg cattggatct     60
ctatactatg gtaatttttt ctgtcacaca tctcaataga cgtgagagga acttctgttt   120
gctgacaaaa agctcacttt ctgacgtcca ctgtagcaga tcgtcctgat caatcaataa   180
agtagtgtta agttaccttaa acatatggtc gttaccttttt atttcatttt aatgagcata  240
acatccatat aagttccaag aaagcaaaac tggtcgtata tccttcagca tggggtcatc   300
accaactgtt ttgccttctt gtccttcttt gttaaggatt aacatgatct ttggtttagt   360
aaacttaaat cattaaatgg atgcaggcaa tggaaattga tcctgataat tcaaccttgt   420
atgcaaagag gagcctttgc tttctgtaca caggcnatga aggaaaggct ttggaggatg   480
ctactaccta cagagatatg caaccagctc ttgctctggt caaggtgggg agtgatacaa   540
atagcataat ctctgtcatg ttccatggtt atttattcgc tctgttgtct ttaggagtat   600
tgcatgacat gcgaagcact cttgcctggc ttgaactcgg attttttaag caaaccaact   660
gacgaagcgt tcgggtaacc tacacttgat tgcttctatt ctttgattga atatttattt   720
gctaaaatat attgttcaaa tacggatatg gaaagaaagt ttgtcatata ttagtaccct   780
aataatatat gattggccaa tgttgaaaat cttttatttttt caattatgtt aggagaaata  840
gctaatcagg aagttaacac ttaaggcttt gttcggttat tcccattaca catggattga   900
atgagattgt aaaaaaattaa gtagtttgac ttgcttgtga tttaaatcca cccaatccca   960
cttaatccat atggattgag agctaaccga attaccgaac aagccaataa agagtttgtc  1020
tgcgtgctta acttgtgctc taagtttcca ccatatttgc agggaaggac aatccgtgaa  1080
gaaaggttat tagtgtacag ggaagaaaga aggttgttac tgcacaggaa aaacagag   1138

<210> SEQ ID NO 28
<211> LENGTH: 32
<212> TYPE: DNA
<213> ORGANISM: Zea mays

<400> SEQUENCE: 28 gctaatttc ttgaaccaat cttttttgac aa                                    32

<210> SEQ ID NO 29
<211> LENGTH: 28
<212> TYPE: DNA
<213> ORGANISM: Zea mays

<400> SEQUENCE: 29
gcaaagtgtc ttaagtttag aggtgtga                                        28

<210> SEQ ID NO 30
<211> LENGTH: 29
<212> TYPE: DNA
```

<213> ORGANISM: Zea mays

<400> SEQUENCE: 30
ctgaggcata catgaaagta gaagattga                              29

<210> SEQ ID NO 31
<211> LENGTH: 20
<212> TYPE: DNA
<213> ORGANISM: Zea mays

<400> SEQUENCE: 31
cctgacctgg cctgttgagt                                         20

<210> SEQ ID NO 32
<211> LENGTH: 21
<212> TYPE: DNA
<213> ORGANISM: Zea mays

<400> SEQUENCE: 32
ctagcaccgg tgaccaaaga a                                       21

<210> SEQ ID NO 33
<211> LENGTH: 19
<212> TYPE: DNA
<213> ORGANISM: Zea mays

<400> SEQUENCE: 33
aggtgaagga cgggtcact                                          19

<210> SEQ ID NO 34
<211> LENGTH: 24
<212> TYPE: DNA
<213> ORGANISM: Zea mays

<400> SEQUENCE: 34
cgttaacaca atcacaggat gaca                                    24

<210> SEQ ID NO 35
<211> LENGTH: 25
<212> TYPE: DNA
<213> ORGANISM: Zea mays

<400> SEQUENCE: 35
gcctaacaga tctcctactg aggtt                                   25

<210> SEQ ID NO 36
<211> LENGTH: 19
<212> TYPE: DNA
<213> ORGANISM: Zea mays

<400> SEQUENCE: 36
ggcgcaacgc aagtacttc                                          19

<210> SEQ ID NO 37
<211> LENGTH: 25
<212> TYPE: DNA
<213> ORGANISM: Zea mays

<400> SEQUENCE: 37
ggtttcagaa gcacatagtg acctt                                   25

<210> SEQ ID NO 38
<211> LENGTH: 20

```
<212> TYPE: DNA
<213> ORGANISM: Zea mays

<400> SEQUENCE: 38
tgctggtgac gtggacaagt                                        20

<210> SEQ ID NO 39
<211> LENGTH: 25
<212> TYPE: DNA
<213> ORGANISM: Zea mays

<400> SEQUENCE: 39
gcctaacaga tctcctactg aggtt                                  25

<210> SEQ ID NO 40
<211> LENGTH: 20
<212> TYPE: DNA
<213> ORGANISM: Zea mays

<400> SEQUENCE: 40
agagaagacg cacgcatcaa                                        20

<210> SEQ ID NO 41
<211> LENGTH: 25
<212> TYPE: DNA
<213> ORGANISM: Zea mays

<400> SEQUENCE: 41
tgtacattgt cgttcacatc ttgct                                  25

<210> SEQ ID NO 42
<211> LENGTH: 21
<212> TYPE: DNA
<213> ORGANISM: Zea mays

<400> SEQUENCE: 42
tgttctgttc acccacttgc a                                      21

<210> SEQ ID NO 43
<211> LENGTH: 18
<212> TYPE: DNA
<213> ORGANISM: Zea mays

<400> SEQUENCE: 43
tggcaaagcc caccactc                                          18

<210> SEQ ID NO 44
<211> LENGTH: 20
<212> TYPE: DNA
<213> ORGANISM: Zea mays

<400> SEQUENCE: 44
ccaaactcct ggtggatcgt                                        20

<210> SEQ ID NO 45
<211> LENGTH: 27
<212> TYPE: DNA
<213> ORGANISM: Zea mays

<400> SEQUENCE: 45
tctactacat tctttagcac gctttcc                                27

<210> SEQ ID NO 46
```

```
<211> LENGTH: 38
<212> TYPE: DNA
<213> ORGANISM: Zea mays

<400> SEQUENCE: 46
tgaacttatt cctatatgaa ttcttaatag aggtcctt                             38

<210> SEQ ID NO 47
<211> LENGTH: 18
<212> TYPE: DNA
<213> ORGANISM: Zea mays

<400> SEQUENCE: 47
atccgttgcg cccagtac                                                   18

<210> SEQ ID NO 48
<211> LENGTH: 33
<212> TYPE: DNA
<213> ORGANISM: Zea mays

<400> SEQUENCE: 48
gcatagcaaa agatatgtat ctaaaaaatt atg                                  33

<210> SEQ ID NO 49
<211> LENGTH: 18
<212> TYPE: DNA
<213> ORGANISM: Zea mays

<400> SEQUENCE: 49
gccgcactcg tagtagca                                                   18

<210> SEQ ID NO 50
<211> LENGTH: 25
<212> TYPE: DNA
<213> ORGANISM: Zea mays

<400> SEQUENCE: 50
catcatggag ggagagaaac gttat                                           25

<210> SEQ ID NO 51
<211> LENGTH: 17
<212> TYPE: DNA
<213> ORGANISM: Zea mays

<400> SEQUENCE: 51
gcggactccg cgaagag                                                    17

<210> SEQ ID NO 52
<211> LENGTH: 23
<212> TYPE: DNA
<213> ORGANISM: Zea mays

<400> SEQUENCE: 52
accctgaggt agaagagcct tac                                             23

<210> SEQ ID NO 53
<211> LENGTH: 19
<212> TYPE: DNA
<213> ORGANISM: Zea mays

<400> SEQUENCE: 53
cctgccggag agagttgct                                                  19
```

```
<210> SEQ ID NO 54
<211> LENGTH: 23
<212> TYPE: DNA
<213> ORGANISM: Zea mays

<400> SEQUENCE: 54
agaggagcct ttgctttctg tac                                              23

<210> SEQ ID NO 55
<211> LENGTH: 19
<212> TYPE: DNA
<213> ORGANISM: Zea mays

<400> SEQUENCE: 55
cagggagggt ttggagctt                                                   19

<210> SEQ ID NO 56
<211> LENGTH: 25
<212> TYPE: DNA
<213> ORGANISM: Zea mays

<400> SEQUENCE: 56
aaaaggatga tagagccaat ttctg                                            25

<210> SEQ ID NO 57
<211> LENGTH: 23
<212> TYPE: DNA
<213> ORGANISM: Zea mays

<400> SEQUENCE: 57
ctgtcggctc ttcctcaaat tga                                              23

<210> SEQ ID NO 58
<211> LENGTH: 25
<212> TYPE: DNA
<213> ORGANISM: Zea mays

<400> SEQUENCE: 58
gcagagggag gagtatttta cttga                                            25

<210> SEQ ID NO 59
<211> LENGTH: 26
<212> TYPE: DNA
<213> ORGANISM: Zea mays

<400> SEQUENCE: 59
gcagggtgca gaaactacat aattaa                                           26

<210> SEQ ID NO 60
<211> LENGTH: 24
<212> TYPE: DNA
<213> ORGANISM: Zea mays

<400> SEQUENCE: 60
ccgtagaata actcggacaa gtgt                                             24

<210> SEQ ID NO 61
<211> LENGTH: 23
<212> TYPE: DNA
<213> ORGANISM: Zea mays

<400> SEQUENCE: 61
gatctcatct tcagctgctt cct                                              23
```

<210> SEQ ID NO 62
<211> LENGTH: 21
<212> TYPE: DNA
<213> ORGANISM: Zea mays

<400> SEQUENCE: 62
ctggtcctct ttgctgtgtc a                                            21

<210> SEQ ID NO 63
<211> LENGTH: 25
<212> TYPE: DNA
<213> ORGANISM: Zea mays

<400> SEQUENCE: 63
caatgaaagc tgttgtagca gagaa                                        25

<210> SEQ ID NO 64
<211> LENGTH: 24
<212> TYPE: DNA
<213> ORGANISM: Zea mays

<400> SEQUENCE: 64
tttgcgtgga ctctaactgc ttat                                         24

<210> SEQ ID NO 65
<211> LENGTH: 20
<212> TYPE: DNA
<213> ORGANISM: Zea mays

<400> SEQUENCE: 65
cgaagcagat atgcggcttt                                              20

<210> SEQ ID NO 66
<211> LENGTH: 21
<212> TYPE: DNA
<213> ORGANISM: Zea mays

<400> SEQUENCE: 66
ctggtcctct ttgctgtgtc a                                            21

<210> SEQ ID NO 67
<211> LENGTH: 22
<212> TYPE: DNA
<213> ORGANISM: Zea mays

<400> SEQUENCE: 67
cccactaatg aacggtctcg at                                           22

<210> SEQ ID NO 68
<211> LENGTH: 23
<212> TYPE: DNA
<213> ORGANISM: Zea mays

<400> SEQUENCE: 68
ccactgttct ccagtcctct tca                                          23

<210> SEQ ID NO 69
<211> LENGTH: 22
<212> TYPE: DNA
<213> ORGANISM: Zea mays

<400> SEQUENCE: 69
caagccacgt ctcaataatc ca                                           22

```
<210> SEQ ID NO 70
<211> LENGTH: 20
<212> TYPE: DNA
<213> ORGANISM: Zea mays

<400> SEQUENCE: 70
tgcgtgccca gcatatactt                                               20

<210> SEQ ID NO 71
<211> LENGTH: 22
<212> TYPE: DNA
<213> ORGANISM: Zea mays

<400> SEQUENCE: 71
tggtatcagc caactgctca tc                                            22

<210> SEQ ID NO 72
<211> LENGTH: 25
<212> TYPE: DNA
<213> ORGANISM: Zea mays

<400> SEQUENCE: 72
agacttcagg aatgagggag tatca                                         25

<210> SEQ ID NO 73
<211> LENGTH: 23
<212> TYPE: DNA
<213> ORGANISM: Zea mays

<400> SEQUENCE: 73
gtatgctaca gtccctccct cta                                           23

<210> SEQ ID NO 74
<211> LENGTH: 21
<212> TYPE: DNA
<213> ORGANISM: Zea mays

<400> SEQUENCE: 74
tgccagtgtc tgtgagctca a                                             21

<210> SEQ ID NO 75
<211> LENGTH: 25
<212> TYPE: DNA
<213> ORGANISM: Zea mays

<400> SEQUENCE: 75
ccttccgact gttcttaatg ttctc                                         25

<210> SEQ ID NO 76
<211> LENGTH: 16
<212> TYPE: DNA
<213> ORGANISM: Zea mays

<400> SEQUENCE: 76
accgacggca cgtgac                                                   16

<210> SEQ ID NO 77
<211> LENGTH: 24
<212> TYPE: DNA
<213> ORGANISM: Zea mays

<400> SEQUENCE: 77
```

```
gcaatggtaa tgaagacggt gaca                                          24

<210> SEQ ID NO 78
<211> LENGTH: 19
<212> TYPE: DNA
<213> ORGANISM: Zea mays

<400> SEQUENCE: 78
cctctcggct cctctccac                                                19

<210> SEQ ID NO 79
<211> LENGTH: 23
<212> TYPE: DNA
<213> ORGANISM: Zea mays

<400> SEQUENCE: 79
aaaacaaagg gcagcgattt agg                                           23

<210> SEQ ID NO 80
<211> LENGTH: 24
<212> TYPE: DNA
<213> ORGANISM: Zea mays

<400> SEQUENCE: 80
ggtcttattt gtgctgtaca tgca                                          24

<210> SEQ ID NO 81
<211> LENGTH: 25
<212> TYPE: DNA
<213> ORGANISM: Zea mays

<400> SEQUENCE: 81
agctggttgc atatctctgt aggta                                         25

<210> SEQ ID NO 82
<211> LENGTH: 14
<212> TYPE: DNA
<213> ORGANISM: Zea mays

<400> SEQUENCE: 82
tggaatcgga accc                                                     14

<210> SEQ ID NO 83
<211> LENGTH: 14
<212> TYPE: DNA
<213> ORGANISM: Zea mays

<400> SEQUENCE: 83
tctgcacaaa atgt                                                     14

<210> SEQ ID NO 84
<211> LENGTH: 19
<212> TYPE: DNA
<213> ORGANISM: Zea mays

<400> SEQUENCE: 84
atttctgtgt gaaggtact                                                19

<210> SEQ ID NO 85
<211> LENGTH: 14
<212> TYPE: DNA
<213> ORGANISM: Zea mays

<400> SEQUENCE: 85
```
acgtgagcga tgat                                                14

<210> SEQ ID NO 86
<211> LENGTH: 19
<212> TYPE: DNA
<213> ORGANISM: Zea mays

<400> SEQUENCE: 86
aagcatctta ttgtttacc                                           19

<210> SEQ ID NO 87
<211> LENGTH: 17
<212> TYPE: DNA
<213> ORGANISM: Zea mays

<400> SEQUENCE: 87
agatctgcta gtccacg                                             17

<210> SEQ ID NO 88
<211> LENGTH: 15
<212> TYPE: DNA
<213> ORGANISM: Zea mays

<400> SEQUENCE: 88
caagggtcac tcact                                               15

<210> SEQ ID NO 89
<211> LENGTH: 20
<212> TYPE: DNA
<213> ORGANISM: Zea mays

<400> SEQUENCE: 89
ataaagcagc taatttgcta                                          20

<210> SEQ ID NO 90
<211> LENGTH: 14
<212> TYPE: DNA
<213> ORGANISM: Zea mays

<400> SEQUENCE: 90
cccacacgat ccaa                                                14

<210> SEQ ID NO 91
<211> LENGTH: 17
<212> TYPE: DNA
<213> ORGANISM: Zea mays

<400> SEQUENCE: 91
agaattgctg gatgcat                                             17

<210> SEQ ID NO 92
<211> LENGTH: 13
<212> TYPE: DNA
<213> ORGANISM: Zea mays

<400> SEQUENCE: 92
ctggacgcaa atc                                                 13

<210> SEQ ID NO 93
<211> LENGTH: 20
<212> TYPE: DNA
<213> ORGANISM: Zea mays

<400> SEQUENCE: 93
ataaagcagc taatttgcta                                              20

<210> SEQ ID NO 94
<211> LENGTH: 13
<212> TYPE: DNA
<213> ORGANISM: Zea mays

<400> SEQUENCE: 94
cgcgaccttc tcg                                                     13

<210> SEQ ID NO 95
<211> LENGTH: 14
<212> TYPE: DNA
<213> ORGANISM: Zea mays

<400> SEQUENCE: 95
cttcgacaaa atgg                                                    14

<210> SEQ ID NO 96
<211> LENGTH: 15
<212> TYPE: DNA
<213> ORGANISM: Zea mays

<400> SEQUENCE: 96
caggttgaac aaaat                                                   15

<210> SEQ ID NO 97
<211> LENGTH: 20
<212> TYPE: DNA
<213> ORGANISM: Zea mays

<400> SEQUENCE: 97
aagcattagt gcattacatc                                              20

<210> SEQ ID NO 98
<211> LENGTH: 14
<212> TYPE: DNA
<213> ORGANISM: Zea mays

<400> SEQUENCE: 98
tcgtcaaaac ttgc                                                    14

<210> SEQ ID NO 99
<211> LENGTH: 16
<212> TYPE: DNA
<213> ORGANISM: Zea mays

<400> SEQUENCE: 99
accacagtag gaatgc                                                  16

<210> SEQ ID NO 100
<211> LENGTH: 16
<212> TYPE: DNA
<213> ORGANISM: Zea mays

<400> SEQUENCE: 100
cagctctcct ttgtcg                                                  16

<210> SEQ ID NO 101
<211> LENGTH: 15
<212> TYPE: DNA
<213> ORGANISM: Zea mays

<400> SEQUENCE: 101
agcagatgtg atccg                                                    15

<210> SEQ ID NO 102
<211> LENGTH: 18
<212> TYPE: DNA
<213> ORGANISM: Zea mays

<400> SEQUENCE: 102
ttggaatgta cagagtac                                                 18

<210> SEQ ID NO 103
<211> LENGTH: 19
<212> TYPE: DNA
<213> ORGANISM: Zea mays

<400> SEQUENCE: 103
ctctgacttg acttttttt                                                19

<210> SEQ ID NO 104
<211> LENGTH: 16
<212> TYPE: DNA
<213> ORGANISM: Zea mays

<400> SEQUENCE: 104
acgaagtaaa caaatc                                                   16

<210> SEQ ID NO 105
<211> LENGTH: 13
<212> TYPE: DNA
<213> ORGANISM: Zea mays

<400> SEQUENCE: 105
cgggactgac ctc                                                      13

<210> SEQ ID NO 106
<211> LENGTH: 15
<212> TYPE: DNA
<213> ORGANISM: Zea mays

<400> SEQUENCE: 106
cggttccttc cttcc                                                    15

<210> SEQ ID NO 107
<211> LENGTH: 15
<212> TYPE: DNA
<213> ORGANISM: Zea mays

<400> SEQUENCE: 107
catgctgtca atgta                                                    15

<210> SEQ ID NO 108
<211> LENGTH: 19
<212> TYPE: DNA
<213> ORGANISM: Zea mays

<400> SEQUENCE: 108
cctttccttc attgcctgt                                                19

<210> SEQ ID NO 109
<211> LENGTH: 15
<212> TYPE: DNA

```
<213> ORGANISM: Zea mays

<400> SEQUENCE: 109
atggaattgg aaccc                                                    15

<210> SEQ ID NO 110
<211> LENGTH: 15
<212> TYPE: DNA
<213> ORGANISM: Zea mays

<400> SEQUENCE: 110
caatctgcat aaaat                                                    15

<210> SEQ ID NO 111
<211> LENGTH: 15
<212> TYPE: DNA
<213> ORGANISM: Zea mays

<400> SEQUENCE: 111
ctgtgtgcag gtact                                                    15

<210> SEQ ID NO 112
<211> LENGTH: 14
<212> TYPE: DNA
<213> ORGANISM: Zea mays

<400> SEQUENCE: 112
cgtgaccgat gatg                                                     14

<210> SEQ ID NO 113
<211> LENGTH: 16
<212> TYPE: DNA
<213> ORGANISM: Zea mays

<400> SEQUENCE: 113
tggtaagcat ctcatt                                                   16

<210> SEQ ID NO 114
<211> LENGTH: 15
<212> TYPE: DNA
<213> ORGANISM: Zea mays

<400> SEQUENCE: 114
atctgctggt ccacg                                                    15

<210> SEQ ID NO 115
<211> LENGTH: 13
<212> TYPE: DNA
<213> ORGANISM: Zea mays

<400> SEQUENCE: 115
aagggccact cac                                                      13

<210> SEQ ID NO 116
<211> LENGTH: 20
<212> TYPE: DNA
<213> ORGANISM: Zea mays

<400> SEQUENCE: 116
ataaagcagc tagtttgcta                                               20

<210> SEQ ID NO 117
<211> LENGTH: 16
```

```
<212> TYPE: DNA
<213> ORGANISM: Zea mays

<400> SEQUENCE: 117
ttcccacatg atccaa                                                    16

<210> SEQ ID NO 118
<211> LENGTH: 17
<212> TYPE: DNA
<213> ORGANISM: Zea mays

<400> SEQUENCE: 118
agaattgctg ggtgcat                                                   17

<210> SEQ ID NO 119
<211> LENGTH: 13
<212> TYPE: DNA
<213> ORGANISM: Zea mays

<400> SEQUENCE: 119
ctggaggcaa atc                                                       13

<210> SEQ ID NO 120
<211> LENGTH: 20
<212> TYPE: DNA
<213> ORGANISM: Zea mays

<400> SEQUENCE: 120
ataaagcagc tagtttgcta                                                20

<210> SEQ ID NO 121
<211> LENGTH: 13
<212> TYPE: DNA
<213> ORGANISM: Zea mays

<400> SEQUENCE: 121
cgcgaccctc tcg                                                       13

<210> SEQ ID NO 122
<211> LENGTH: 15
<212> TYPE: DNA
<213> ORGANISM: Zea mays

<400> SEQUENCE: 122
cttcgataaa atggc                                                     15

<210> SEQ ID NO 123
<211> LENGTH: 15
<212> TYPE: DNA
<213> ORGANISM: Zea mays

<400> SEQUENCE: 123
caggttcaac aaaat                                                     15

<210> SEQ ID NO 124
<211> LENGTH: 19
<212> TYPE: DNA
<213> ORGANISM: Zea mays

<400> SEQUENCE: 124
agcattagtg cactacatc                                                 19

<210> SEQ ID NO 125
```

-continued

```
<211> LENGTH: 13
<212> TYPE: DNA
<213> ORGANISM: Zea mays

<400> SEQUENCE: 125
cgtcaaaatt tgc                                                          13

<210> SEQ ID NO 126
<211> LENGTH: 15
<212> TYPE: DNA
<213> ORGANISM: Zea mays

<400> SEQUENCE: 126
ccacagtaag aatgc                                                        15

<210> SEQ ID NO 127
<211> LENGTH: 15
<212> TYPE: DNA
<213> ORGANISM: Zea mays

<400> SEQUENCE: 127
agctctccgt tgtcg                                                        15

<210> SEQ ID NO 128
<211> LENGTH: 14
<212> TYPE: DNA
<213> ORGANISM: Zea mays

<400> SEQUENCE: 128
agcagacgtg atcc                                                         14

<210> SEQ ID NO 129
<211> LENGTH: 21
<212> TYPE: DNA
<213> ORGANISM: Zea mays

<400> SEQUENCE: 129
aatttggaat gtatagagta c                                                 21

<210> SEQ ID NO 130
<211> LENGTH: 17
<212> TYPE: DNA
<213> ORGANISM: Zea mays

<400> SEQUENCE: 130
ctgacttgac ctttttt                                                      17

<210> SEQ ID NO 131
<211> LENGTH: 15
<212> TYPE: DNA
<213> ORGANISM: Zea mays

<400> SEQUENCE: 131
cgaagtagac aaatc                                                        15

<210> SEQ ID NO 132
<211> LENGTH: 13
<212> TYPE: DNA
<213> ORGANISM: Zea mays

<400> SEQUENCE: 132
cgggagtgac ctc                                                          13
```

```
<210> SEQ ID NO 133
<211> LENGTH: 16
<212> TYPE: DNA
<213> ORGANISM: Zea mays

<400> SEQUENCE: 133 acgtttctt ccttcc                                                           16

<210> SEQ ID NO 134
<211> LENGTH: 16
<212> TYPE: DNA
<213> ORGANISM: Zea mays

<400> SEQUENCE: 134
tgctgtcgat gtagtc                                                          16

<210> SEQ ID NO 135
<211> LENGTH: 18
<212> TYPE: DNA
<213> ORGANISM: Zea mays

<400> SEQUENCE: 135
ctttccttca tagcctgt                                                        18

<210> SEQ ID NO 136
<211> LENGTH: 201
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t

<400> SEQUENCE: 136
aaccntagaa tactaagaat tttgaatctt ataattgagt acgtatttgc aggaaccgag           60
ttaatgtgga ggacgaggag acactttcaa gcgttgctca ntgtattgag caactacgac         120
agagttcttc atcctcacag ganaaagaga gctctttgaa gcagttatta gatcttgttc         180
aaactcgtga tactgcattc g                                                   201

<210> SEQ ID NO 137
<211> LENGTH: 201
<212> TYPE: DNA
<213> ORGANISM: Zea mays
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
```

<400> SEQUENCE: 137
tagaattgga gtctgtgagg ncggagccac aggctccttt ggaagactac aggtaaatga    60
agtattacat ttcgacatat gattggattc atacgatgaa naaagaccct tagcttgttt   120
ctgctaatcc ataattccat accgagtttt gacgtactca nttgattcaa aagattattt   180
atgccattca tacccatang a                                              201

<210> SEQ ID NO 138
<211> LENGTH: 575
<212> TYPE: DNA
<213> ORGANISM: Zea mays
<220> FEATURE:
<221> NAME/KEY: misc_feature
<222> LOCATION: (67)..(69)
<223> OTHER INFORMATION: n is a, c, g, or t
<220> FEATURE:
<221> NAME/KEY: misc_feature
<222> LOCATION: (140)..(142)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (525)..(528)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t

<400> SEQUENCE: 138 taccctgcc tgcaccggtc accggcctcg aacgcctcga ggcagaccgc gcagtccccg     60
gtctctnnnc cgtctgcggc agccttgaag tactcatggc aaggaagcgt agcgagctcg   120
ccgctggaca gtccccggcn nncgcggccg tcctctacgc gntcctcctg gttggcggcg   180
tgctggctgc tgccgcggga gccgagcccc cgcagcagag cccagaaaac gacgaggatg   240
tgggcgacga gcatcacagc gacgcccgcg atgagcagca ccacggagag gatcgcggtt   300
gggttggtcg tcgtcatgct gttgctatgg tagcgcgttg tagctagcta gtgatgaatc   360
atgtnactaa nggtcgtgtt tctcatcgat catgtgaaga tttctcttgc ttttgacgtt   420
ccttggtttg gatttggata catatgtaga ccagttcnag tanatntgtt gggagaaacc   480
aaagaagtgt ggcgacgacc tcttattgtc anttcagcac tgtannnggg ggntgtgcgt   540
agctgcgagt cactgatagc tacaagcaag aaaac          575

<210> SEQ ID NO 139
<211> LENGTH: 201
<212> TYPE: DNA
<213> ORGANISM: Zea mays
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 139
gtttcaaatt aatgtngaga aagtcaaata tttatagagg acgtaagaag acgggacatc    60
acattacttg aagctcgccc ttgtactcgt ggtaaaagtg ngctctgttt ctcatcgtca    120
agaagaaaag acagaaagaa agcaagaaaa caaggccaaa aggagcctac gatgaatcca    180
tcgtcaacga agcgtcaatg g                                             201

<210> SEQ ID NO 140
<211> LENGTH: 487
<212> TYPE: DNA
<213> ORGANISM: Zea mays
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (232)..(232)

<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (256)..(428)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t

<400> SEQUENCE: 140

```
actactgatg ccattggcta ccatgaaccc atggatgcag tactgcatga agcaacaggg    60
ggttgccaac ttgntagcgt ggccgaccct gatgntgcag caacngttgg cctcaccgnt   120
tcagcngtgc cagatgccaa tgatgatgcc nggtatgatg ccaccgatgn cnatgatgcc   180
gatgccgant atgatgncat cnatgatggt gccgactatg atgtcaccaa tnacgatngc   240
tagtatgatg ccnccnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnca gtgccacaat gttactctga ttcnatctcg cacattatac aacaacaaca   480
attacca                                                             487
```

<210> SEQ ID NO 141
<211> LENGTH: 374
<212> TYPE: DNA
<213> ORGANISM: Zea mays
<220> FEATURE:
<221> NAME/KEY: misc_feature
<222> LOCATION: (130)..(130)
<223> OTHER INFORMATION: n is a, c, g, or t

<400> SEQUENCE: 141

```
tctgctgttc aagaaaatgc tggcattaaa ggtttggcct accaatgcga cgtattcttg    60
catcctgaag gtgtttgata cgcccgattt gctatccgtt ggaatgcaac ttcatggctg   120
cttgctgaan atgggaacgg aggttgacac tgctttgggg actgccttga tgacgatgta   180
tggcaggtgt ggtggagttg atgagatacc taggttggct tgtcgtataa ggcatgatgc   240
gctttcgagg actgccctgc ttggcgctta tgcacgtact ggatacaatg cagaggcaat   300
tggtgttttc aaggagatga tcatgaaaaa tatggcaatt gaccagtcag ctatgactgg   360
tatgctgcag gttt                                                    374
```

<210> SEQ ID NO 142
<211> LENGTH: 733
<212> TYPE: DNA
<213> ORGANISM: Zea mays
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature

```
<222> LOCATION: (571)..(571)
<223> OTHER INFORMATION: n is a, c, g, or t
<220> FEATURE:
<221> NAME/KEY: misc_feature
<222> LOCATION: (582)..(584)
<223> OTHER INFORMATION: n is a, c, g, or t
<220> FEATURE:
<221> NAME/KEY: misc_feature
<222> LOCATION: (586)..(594)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (615)..(618)
<223> OTHER INFORMATION: n is a, c, g, or t
<220> FEATURE:
<221> NAME/KEY: misc_feature
<222> LOCATION: (625)..(632)
<223> OTHER INFORMATION: n is a, c, g, or t
<220> FEATURE:
<221> NAME/KEY: misc_feature
<222> LOCATION: (634)..(652)
<223> OTHER INFORMATION: n is a, c, g, or t
<220> FEATURE:
<221> NAME/KEY: misc_feature
<222> LOCATION: (656)..(659)
<223> OTHER INFORMATION: n is a, c, g, or t
<220> FEATURE:
<221> NAME/KEY: misc_feature
<222> LOCATION: (663)..(665)
<223> OTHER INFORMATION: n is a, c, g, or t
<220> FEATURE:
<221> NAME/KEY: misc_feature
<222> LOCATION: (671)..(672)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (681)..(691)
<223> OTHER INFORMATION: n is a, c, g, or t
<220> FEATURE:
<221> NAME/KEY: misc_feature
<222> LOCATION: (693)..(696)
<223> OTHER INFORMATION: n is a, c, g, or t
<220> FEATURE:
<221> NAME/KEY: misc_feature
<222> LOCATION: (698)..(708)
<223> OTHER INFORMATION: n is a, c, g, or t
<220> FEATURE:
<221> NAME/KEY: misc_feature
<222> LOCATION: (710)..(712)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (718)..(722)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
```

```
<221> NAME/KEY: misc_feature
<222> LOCATION: (727)..(732)
<223> OTHER INFORMATION: n is a, c, g, or t

<400> SEQUENCE: 142
caagttctga gtttctctct tgtcagtcaa tggcttgggt aaaaattgtg aacagagaat    60
atgaaagcct gacaaactag caatgagtcc attttctgaa gataaacagc aaggaaaatt   120
ctgaatccca tgtgtagaaa catgtaggaa acacctttct tgtttatgag tgataggcaa   180
aattttggtc attgcatcct agggttaact tacagtcttc ttttgcaggt caaggacact   240
cccacgaagt gttctgatca tagggaccca agcggtgatg ataattactt acctgctctt   300
tgcattgggc cggctcgcca cactttacgt ctctgtcgcc ttactcgggn tatgttttgg   360
tatctcgctc tccgtgataa tctcaacctc ctcagagctc ttcggactna agcactttgg   420
aaagatattc aacttcatcg cattggcgaa tccggtaggc gcgttcctgt ttaacaccct   480
cgcgggatat gtctacgatc tcgaagtgga aaagcagcac gccacaacat cagggtcgga   540
cgttgcatgt catggcccta attgcttcag nctaacattc tnnntnnnnn nnnncgtngc   600
atgcntgggc acacnnnnga gcacnnnnnn nncnnnnnnn nnnnnnnnnn nntatnnnnt   660
gcnnnatgca nncggntcnt nnnnnnnnnn nannnncnnn nnnnnnnnan nnatgncnnn   720
nnagntnnnn nnt                                                      733

<210> SEQ ID NO 143
<211> LENGTH: 201
<212> TYPE: DNA
<213> ORGANISM: Zea mays
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 143
ttgataatga tttcatatct cggtaggttg aagatattgt tgacacaggg aatactctnt    60
cctatctcat tgctcatttg gagaagaaag gtgcatcatc natatcggtt tgcacttttc   120
ttgacaaacc agcaagaagg aaagtcaatg ttcatctagt aggggatgga aaattttacc   180
gtggatttga ggtaccagta c                                             201

<210> SEQ ID NO 144
<211> LENGTH: 201
<212> TYPE: DNA
<213> ORGANISM: Zea mays
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t

<400> SEQUENCE: 144
ctagattttg tgaagcccca tcagcatagt ggaccgcgaa atattcctca gcatctttcc    60
gtaccccctt ggcacctngg accattgcgg ttgtagccct ncaacatata gcacatatct   120
```

```
caaaagccaa ggtaaaggag accctgttgg tggtggtggt cgtcgtnggt gactcaggtg    180
ggatagattc cctggtgtgt g                                              201

<210> SEQ ID NO 145
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 145
gaaggccaga cagaagcaga ccaaacaacc aaggtccacc aaacgtgtat atcagctctt     60
caagggcagt aaaacagtga ggcatgctat atctatcaga nacgcatttg tatgggcatg    120
ggggttcagc aacacctcct gccaaaaaac ataatgttaa gtttataaca tcaggcaaac    180
tgaaaaacgt tacatagtta a                                              201

<210> SEQ ID NO 146
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 146
tgcttgatac agcataaatc catcgcccag ctgaaactaa aaccaagttg tcattggcca     60
ctttattgtt tgactgcaaa gaataaaggc acgtcactca ngagaagtgc tataggaaac    120
atcaattgca ttatttatca acttatgatn tctcagaaan tagaaaatgc attgtgcgca    180
cagaccataa catgcanctg t                                              201

<210> SEQ ID NO 147
<211> LENGTH: 515
<212> TYPE: DNA
<213> ORGANISM: Zea mays
<220> FEATURE:
<221> NAME/KEY: misc_feature
<222> LOCATION: (102)..(102)
<223> OTHER INFORMATION: n is a, c, g, or t

<400> SEQUENCE: 147
tattacgaga aaagtagatc tggtagtgca gaaaggggg cactaattag tcattacatt     60
tactaattta catatagaac gtcagctgat ttaggcttat tntatacaga tacgatggtg    120
acatgaggtt atccaccata cacatgataa agatctagga tagattccaa caacaacaaa    180
aaaaactgga agacacgatg ctgtttttact gagtgtgcac ggattattgc tttcagtttc    240
catgatggaa gaaatgaaac accaaaaaag atctacagat ggttattttg ccttctcagt    300
```

```
ccggttcatc acatcatggt aatataatag aacacacatt ggctgcccgt atatgcagaa      360
aaaaaaccaa aagatcatat tgccaaccta ttgaatatac cacaaattag acaggttccc      420
ataaaaaacg atcctagcaa gtatcaacta agaaaaatat ggctcaccat tgtgtcactg      480
aatttatttt tgaggtatga tgtcaatatg atgag                                 515
```

```
<210> SEQ ID NO 148
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t

<400> SEQUENCE: 148
cgatctcctc atgcatgctg ataaatagtc tgagtcgccc ctcgtcgacc tttaataata      60
atagtcttcg ataagattag gctgcctata cacacacgtc ncccgtcgcg ttatttctag     120
tacaacggag caagctagct agcgcgcttt gaccactnaa tcattagctt agagcgcact     180
gtagcagcaa gttcacgcgc g                                                201
```

```
<210> SEQ ID NO 149
<211> LENGTH: 601
<212> TYPE: DNA
<213> ORGANISM: Zea mays
<220> FEATURE:
<221> NAME/KEY: misc_feature
<222> LOCATION: (179)..(179)
<223> OTHER INFORMATION: n is a, c, g, or t

<400> SEQUENCE: 149
tctgccgatg gttcaccggt tccattatca tctcccctg accctagggt gcctgattga      60
accaattgaa attgatcgtc aacccaagta ggaaactctc tgaatgagtt tgtacgtgga     120
tcgacagctt tcttaaactt tcctatgcgt atctcataca tgttacgcac atcaatgang     180
acctgtcaca ttaatagcgt aaacaattcg caggcaatgg aaaagaagtt caacaatgca     240
aagatagatg acgagttatg aactatctga gatagatgaa acacttacag tgtctggatc     300
acttatcaag tcattccagt cttttggctt aacatatttc ccaacgattt tagttggcat     360
aacacctggg tctccaaacg tcactatcta caaaatggcc aaggagcaga ctaagctgga     420
ccgtttcatc attaaatatc cagtgaccaa ccaacaagaa ccatgcaggc aaactaacct     480 ccttttcaa tttgacacgg acatgatccc atcggaatgg tgcatcttcc ccagcaccaa      540
caggggagtg actggtatgt ccatgatgta tggcctcatc ctctggagta acaggtgact     600
g                                                                      601
```

```
<210> SEQ ID NO 150
<211> LENGTH: 996
<212> TYPE: DNA
<213> ORGANISM: Zea mays
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (944)..(944)
<223> OTHER INFORMATION: n is a, c, g, or t
```

<400> SEQUENCE: 150

```
tgagatctac agcagaaacc cctcctgctc acacatattc aaatatatta gcttttcaag        60
tcatatataa aatttaaaat gtagaactaa aataaacttg acacattatt aacaaaaaca       120
cctaacgctt ttatataaca tggtcaggaa aaaaatgtgt aaatggttat gcaattgtgt       180
cttaatatct aattttttcg ttccctcaaa tcactgtgat ctactaacat gagtcgaaca       240
ctaatacttg catgtaatag tgatatacct tccgcaatga attgatgagg gtgccgagtg       300
ggggagagtt aacttttgct cgtctcgaaa tctgaatttg attggaaaaa atagaatcgg       360
tgcatgatta aattttgcta agccagtaaa tgaaccaagc agattgatga atgagtgaat       420
attgaactcc aagacatacc tcatcaagtc ttatatatcc aggaggcaac ctcgggtcac       480
tctcttcaat catcatgcca agaagttttt ccaaagagac accattttca attgtgcatg       540
cccatcccca ttcgttggcc aagcctagca tttcggtaag gaaagaggca tcgtggagag       600
gacctgtcca aagtgggcct acaacagtga ttgaatcggc atcctgtgaa aaagggacaa       660
ttatatacta gcacagttcc atggccaagt actccaaaaa caacgcaact cgatcaggtt       720
tcttgcatgg cataggcata caattancat cgaagattat tcattagtaa accaacatca       780
gggttagcta caaatgatat cgttccttaa atgacacttg agtacttgac tcctatgtta       840
ttttgtgtta attaatactg acaaagttaa atggttaggg cctaagtttc ctgaatcaac       900
caccagtaat aaaacaacaa tttagtcctg ccacaatgat ccantgtacc tactgttgtg       960
tctgtacatc cacaagaaat ctgccccagc tcatca                                 996
```

<210> SEQ ID NO 151
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t

<400> SEQUENCE: 151

```
tatcatgtat gcgatgatct gccagcgtga ggacattctg acagttttaa acttttttgt        60
attcatggta tgcatgttgt gcattggttc tacataacat natacaagca aaactcaata       120
caaatctnaa aaaaccaga ttaagaaata ttaggtatac tctattttac angtataacc        180
aaagaactaa ctccatatat g                                                 201
```

<210> SEQ ID NO 152
<211> LENGTH: 201
<212> TYPE: DNA
<213> ORGANISM: Zea mays
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:

<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t

<400> SEQUENCE: 152
agaattgcta ccatgcatnt tggggtcctg ctatgtattg ggttcantct atggagaata    60
gaatcaagga actgagttgg gaagcgcttt gtgccaccct naacactaga tagatcagca   120
taacctgctc attagacatt tttatcacat ccatcaaacc aacttagtaa ccnaatatgt   180
ggaacaattt gaccaactta t                                             201

<210> SEQ ID NO 153
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t

<400> SEQUENCE: 153
aaatttactt aaccaaagat ctgtatgagt tatcaggttg aagacggata actcaacagc    60
aagacaatgg aagaaaacaa ggactgcatg tgacagatgg ntgatacaaa atagtagtag   120
tgcaagcact catccctttg tcnaaagttt cagaatctac ttggttccta ttgcaccaaa   180
aaaaacaagg taaaaatctt g                                             201

<210> SEQ ID NO 154
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t

<400> SEQUENCE: 154
ttagagacta atctttaacc cctctaacca aacaccatct aaattaaatt aggtcgcaat    60
acatgattta ggactccttg gagttgctct aacgttccca nttgtcggac gccttcagta   120
tcnggttggn cattttaaca aagcaagtgc attcgagaga cccattttta caagttcgat   180
gagagtcggc ctattttaga g                                             201

<210> SEQ ID NO 155
<211> LENGTH: 23
<212> TYPE: DNA
<213> ORGANISM: Zea mays

<400> SEQUENCE: 155
gaggacgagg agacactttc aag                                            23

<210> SEQ ID NO 156
<211> LENGTH: 35
<212> TYPE: DNA
<213> ORGANISM: Zea mays

<400> SEQUENCE: 156
ggtaaatgaa gtattacatt tcgacatatg attgg        35

<210> SEQ ID NO 157
<211> LENGTH: 17
<212> TYPE: DNA
<213> ORGANISM: Zea mays

<400> SEQUENCE: 157
gctcgccgct ggacagt        17

<210> SEQ ID NO 158
<211> LENGTH: 21
<212> TYPE: DNA
<213> ORGANISM: Zea mays

<400> SEQUENCE: 158
ttgaagctcg cccttgtact c        21

<210> SEQ ID NO 159
<211> LENGTH: 22
<212> TYPE: DNA
<213> ORGANISM: Zea mays

<400> SEQUENCE: 159
tgaacccatg gatgcagtac tg        22

<210> SEQ ID NO 160
<211> LENGTH: 23
<212> TYPE: DNA
<213> ORGANISM: Zea mays

<400> SEQUENCE: 160
cgatttgcta tccgttggaa tgc        23

<210> SEQ ID NO 161
<211> LENGTH: 24
<212> TYPE: DNA
<213> ORGANISM: Zea mays

<400> SEQUENCE: 161
cgtgataatc tcaacctcct caga        24

<210> SEQ ID NO 162
<211> LENGTH: 28
<212> TYPE: DNA
<213> ORGANISM: Zea mays

<400> SEQUENCE: 162
ggttgaagat attgttgaca cagggaat        28

<210> SEQ ID NO 163
<211> LENGTH: 24
<212> TYPE: DNA
<213> ORGANISM: Zea mays

<400> SEQUENCE: 163
cgcgaaatat tcctcagcat cttt        24

<210> SEQ ID NO 164
<211> LENGTH: 25
<212> TYPE: DNA
<213> ORGANISM: Zea mays

<400> SEQUENCE: 164
gcagtaaaac agtgaggcat gctat        25

<210> SEQ ID NO 165
<211> LENGTH: 24
<212> TYPE: DNA
<213> ORGANISM: Zea mays

<400> SEQUENCE: 165
ggccacttta ttgtttgact gcaa        24

<210> SEQ ID NO 166
<211> LENGTH: 27
<212> TYPE: DNA
<213> ORGANISM: Zea mays

<400> SEQUENCE: 166
aaaagtagat ctggtagtgc agaaagg        27

<210> SEQ ID NO 167
<211> LENGTH: 27
<212> TYPE: DNA
<213> ORGANISM: Zea mays

<400> SEQUENCE: 167
agtcttcgat aagattaggc tgcctat        27

<210> SEQ ID NO 168
<211> LENGTH: 27
<212> TYPE: DNA
<213> ORGANISM: Zea mays

<400> SEQUENCE: 168
cgacagcttt cttaaacttt cctatgc        27

<210> SEQ ID NO 169
<211> LENGTH: 22
<212> TYPE: DNA
<213> ORGANISM: Zea mays

<400> SEQUENCE: 169
caggtttctt gcatggcata gg        22

<210> SEQ ID NO 170
<211> LENGTH: 23
<212> TYPE: DNA
<213> ORGANISM: Zea mays

<400> SEQUENCE: 170
gcatgttgtg cattggttct aca        23

<210> SEQ ID NO 171
<211> LENGTH: 20
<212> TYPE: DNA
<213> ORGANISM: Zea mays

<400> SEQUENCE: 171

```
ctgagttggg aagcgctttg                                              20

<210> SEQ ID NO 172
<211> LENGTH: 25
<212> TYPE: DNA
<213> ORGANISM: Zea mays

<400> SEQUENCE: 172
caatggaaga aaacaaggac tgcat                                        25

<210> SEQ ID NO 173
<211> LENGTH: 27
<212> TYPE: DNA
<213> ORGANISM: Zea mays

<400> SEQUENCE: 173
gcaatacatg atttaggact ccttgga                                      27

<210> SEQ ID NO 174
<211> LENGTH: 25
<212> TYPE: DNA
<213> ORGANISM: Zea mays

<400> SEQUENCE: 174
tgaggatgaa gaactctgtc gtagt                                        25

<210> SEQ ID NO 175
<211> LENGTH: 28
<212> TYPE: DNA
<213> ORGANISM: Zea mays

<400> SEQUENCE: 175
tggaattatg gattagcaga aacaagct                                     28

<210> SEQ ID NO 176
<211> LENGTH: 15
<212> TYPE: DNA
<213> ORGANISM: Zea mays

<400> SEQUENCE: 176
agcacgccgc caacc                                                   15

<210> SEQ ID NO 177
<211> LENGTH: 27
<212> TYPE: DNA
<213> ORGANISM: Zea mays

<400> SEQUENCE: 177
ccttgttttc ttgctttctt tctgtct                                      27

<210> SEQ ID NO 178
<211> LENGTH: 21
<212> TYPE: DNA
<213> ORGANISM: Zea mays

<400> SEQUENCE: 178
ccaacagttg ctgcatcatc a                                            21

<210> SEQ ID NO 179
<211> LENGTH: 20
<212> TYPE: DNA
<213> ORGANISM: Zea mays
```

```
<400> SEQUENCE: 179
ccccaaagca gtgtcaacct                                              20

<210> SEQ ID NO 180
<211> LENGTH: 20
<212> TYPE: DNA
<213> ORGANISM: Zea mays

<400> SEQUENCE: 180
gccaatgcga tgaagttgaa                                              20

<210> SEQ ID NO 181
<211> LENGTH: 24
<212> TYPE: DNA
<213> ORGANISM: Zea mays

<400> SEQUENCE: 181
ctttccttct tgctggtttg tcaa                                         24

<210> SEQ ID NO 182
<211> LENGTH: 25
<212> TYPE: DNA
<213> ORGANISM: Zea mays

<400> SEQUENCE: 182
ggtctccttt accttggctt ttgag                                        25

<210> SEQ ID NO 183
<211> LENGTH: 19
<212> TYPE: DNA
<213> ORGANISM: Zea mays

<400> SEQUENCE: 183
gcaggaggtg ttgctgaac                                               19

<210> SEQ ID NO 184
<211> LENGTH: 23
<212> TYPE: DNA
<213> ORGANISM: Zea mays

<400> SEQUENCE: 184
ctgtgcgcac aatgcatttt cta                                          23

<210> SEQ ID NO 185
<211> LENGTH: 25
<212> TYPE: DNA
<213> ORGANISM: Zea mays

<400> SEQUENCE: 185
ggataacctc atgtcaccat cgtat                                        25

<210> SEQ ID NO 186
<211> LENGTH: 22
<212> TYPE: DNA
<213> ORGANISM: Zea mays

<400> SEQUENCE: 186
gctagcttgc tccgttgtac ta                                           22

<210> SEQ ID NO 187
<211> LENGTH: 23
<212> TYPE: DNA
<213> ORGANISM: Zea mays
```

```
<400> SEQUENCE: 187
tttccattgc ctgcgaattg ttt                                          23

<210> SEQ ID NO 188
<211> LENGTH: 25
<212> TYPE: DNA
<213> ORGANISM: Zea mays

<400> SEQUENCE: 188
atttgtagct aaccctgatg ttggt                                        25

<210> SEQ ID NO 189
<211> LENGTH: 38
<212> TYPE: DNA
<213> ORGANISM: Zea mays

<400> SEQUENCE: 189
tgtaaaatag agtataccta atatttctta atctggtt                          38

<210> SEQ ID NO 190
<211> LENGTH: 26
<212> TYPE: DNA
<213> ORGANISM: Zea mays

<400> SEQUENCE: 190
gtctaatgag caggttatgc tgatct                                       26

<210> SEQ ID NO 191
<211> LENGTH: 21
<212> TYPE: DNA
<213> ORGANISM: Zea mays

<400> SEQUENCE: 191
acaaagggat gagtgcttgc a                                            21

<210> SEQ ID NO 192
<211> LENGTH: 25
<212> TYPE: DNA
<213> ORGANISM: Zea mays

<400> SEQUENCE: 192
ctctcgaatg cacttgcttt gttaa                                        25

<210> SEQ ID NO 193
<211> LENGTH: 17
<212> TYPE: DNA
<213> ORGANISM: Zea mays

<400> SEQUENCE: 193
cgttgctcaa tgtattg                                                 17

<210> SEQ ID NO 194
<211> LENGTH: 16
<212> TYPE: DNA
<213> ORGANISM: Zea mays

<400> SEQUENCE: 194
acgatgaaga aagacc                                                  16

<210> SEQ ID NO 195
<211> LENGTH: 15
<212> TYPE: DNA
```

```
<213> ORGANISM: Zea mays

<400> SEQUENCE: 195
aggaggagcg cgtag                                                      15

<210> SEQ ID NO 196
<211> LENGTH: 14
<212> TYPE: DNA
<213> ORGANISM: Zea mays

<400> SEQUENCE: 196
cagagcgcac tttt                                                       14

<210> SEQ ID NO 197
<211> LENGTH: 14
<212> TYPE: DNA
<213> ORGANISM: Zea mays

<400> SEQUENCE: 197
acgctagcaa gttg                                                       14

<210> SEQ ID NO 198
<211> LENGTH: 17
<212> TYPE: DNA
<213> ORGANISM: Zea mays

<400> SEQUENCE: 198
cttgctgaaa atgggaa                                                    17

<210> SEQ ID NO 199
<211> LENGTH: 16
<212> TYPE: DNA
<213> ORGANISM: Zea mays

<400> SEQUENCE: 199
cggactaaag cacttt                                                     16

<210> SEQ ID NO 200
<211> LENGTH: 19
<212> TYPE: DNA
<213> ORGANISM: Zea mays

<400> SEQUENCE: 200
caaaccgata tggatgatg                                                  19

<210> SEQ ID NO 201
<211> LENGTH: 14
<212> TYPE: DNA
<213> ORGANISM: Zea mays

<400> SEQUENCE: 201
agccctgcaa cata                                                       14

<210> SEQ ID NO 202
<211> LENGTH: 20
<212> TYPE: DNA
<213> ORGANISM: Zea mays

<400> SEQUENCE: 202
catacaaatg cgtgtctgat                                                 20

<210> SEQ ID NO 203
<211> LENGTH: 17
```

```
<212> TYPE: DNA
<213> ORGANISM: Zea mays

<400> SEQUENCE: 203
acgtcactca ggagaag                                                    17

<210> SEQ ID NO 204
<211> LENGTH: 22
<212> TYPE: DNA
<213> ORGANISM: Zea mays

<400> SEQUENCE: 204
ctgatttagg cttattatat ac                                              22

<210> SEQ ID NO 205
<211> LENGTH: 15
<212> TYPE: DNA
<213> ORGANISM: Zea mays

<400> SEQUENCE: 205
cacacgtcgc ccgtc                                                      15

<210> SEQ ID NO 206
<211> LENGTH: 15
<212> TYPE: DNA
<213> ORGANISM: Zea mays

<400> SEQUENCE: 206
caggtcgtca ttgat                                                      15

<210> SEQ ID NO 207
<211> LENGTH: 17
<212> TYPE: DNA
<213> ORGANISM: Zea mays

<400> SEQUENCE: 207
tcttcgatgg taattgt                                                    17

<210> SEQ ID NO 208
<211> LENGTH: 23
<212> TYPE: DNA
<213> ORGANISM: Zea mays

<400> SEQUENCE: 208
tgagttttgc ttgtattatg tta                                             23

<210> SEQ ID NO 209
<211> LENGTH: 17
<212> TYPE: DNA
<213> ORGANISM: Zea mays

<400> SEQUENCE: 209
tgccaccctg aacacta                                                    17

<210> SEQ ID NO 210
<211> LENGTH: 18
<212> TYPE: DNA
<213> ORGANISM: Zea mays

<400> SEQUENCE: 210
tgacagatgg ctgataca                                                   18

<210> SEQ ID NO 211
```

```
<211> LENGTH: 16
<212> TYPE: DNA
<213> ORGANISM: Zea mays

<400> SEQUENCE: 211
tccgacaagt gggaac                                                   16

<210> SEQ ID NO 212
<211> LENGTH: 17
<212> TYPE: DNA
<213> ORGANISM: Zea mays

<400> SEQUENCE: 212
cgttgctcag tgtattg                                                  17

<210> SEQ ID NO 213
<211> LENGTH: 16
<212> TYPE: DNA
<213> ORGANISM: Zea mays

<400> SEQUENCE: 213
acgatgaaaa aagacc                                                   16

<210> SEQ ID NO 214
<211> LENGTH: 15
<212> TYPE: DNA
<213> ORGANISM: Zea mays

<400> SEQUENCE: 214
aggaggaccg cgtag                                                    15

<210> SEQ ID NO 215
<211> LENGTH: 17
<212> TYPE: DNA
<213> ORGANISM: Zea mays

<400> SEQUENCE: 215
aaacagagct cactttt                                                  17

<210> SEQ ID NO 216
<211> LENGTH: 14
<212> TYPE: DNA
<213> ORGANISM: Zea mays

<400> SEQUENCE: 216
cgctaacaag ttgg                                                     14

<210> SEQ ID NO 217
<211> LENGTH: 17
<212> TYPE: DNA
<213> ORGANISM: Zea mays

<400> SEQUENCE: 217
cttgctgaag atgggaa                                                  17

<210> SEQ ID NO 218
<211> LENGTH: 13
<212> TYPE: DNA
<213> ORGANISM: Zea mays

<400> SEQUENCE: 218
cggactcaag cac                                                      13
```

```
<210> SEQ ID NO 219
<211> LENGTH: 19
<212> TYPE: DNA
<213> ORGANISM: Zea mays

<400> SEQUENCE: 219
caaaccgata tagatgatg                                                  19

<210> SEQ ID NO 220
<211> LENGTH: 17
<212> TYPE: DNA
<213> ORGANISM: Zea mays

<400> SEQUENCE: 220
tgtagcccta caacata                                                    17

<210> SEQ ID NO 221
<211> LENGTH: 20
<212> TYPE: DNA
<213> ORGANISM: Zea mays

<400> SEQUENCE: 221
catacaaatg cgtttctgat                                                 20

<210> SEQ ID NO 222
<211> LENGTH: 17
<212> TYPE: DNA
<213> ORGANISM: Zea mays

<400> SEQUENCE: 222
acgtcactca agagaag                                                    17

<210> SEQ ID NO 223
<211> LENGTH: 22
<212> TYPE: DNA
<213> ORGANISM: Zea mays

<400> SEQUENCE: 223
ctgatttagg cttattgtat ac                                              22

<210> SEQ ID NO 224
<211> LENGTH: 15
<212> TYPE: DNA
<213> ORGANISM: Zea mays

<400> SEQUENCE: 224
cacacgtcac ccgtc                                                      15

<210> SEQ ID NO 225
<211> LENGTH: 16
<212> TYPE: DNA
<213> ORGANISM: Zea mays

<400> SEQUENCE: 225
acaggtcatc attgat                                                     16

<210> SEQ ID NO 226
<211> LENGTH: 18
<212> TYPE: DNA
<213> ORGANISM: Zea mays

<400> SEQUENCE: 226
atcttcgatg ataattgt                                                   18
```

```
<210> SEQ ID NO 227
<211> LENGTH: 21
<212> TYPE: DNA
<213> ORGANISM: Zea mays

<400> SEQUENCE: 227
agttttgctt gtataatgtt a                                              21

<210> SEQ ID NO 228
<211> LENGTH: 17
<212> TYPE: DNA
<213> ORGANISM: Zea mays

<400> SEQUENCE: 228 tgccaccctα aacacta                                                   17

<210> SEQ ID NO 229
<211> LENGTH: 18
<212> TYPE: DNA
<213> ORGANISM: Zea mays

<400> SEQUENCE: 229
tgacagatgg atgataca                                                  18

<210> SEQ ID NO 230
<211> LENGTH: 16
<212> TYPE: DNA
<213> ORGANISM: Zea mays

<400> SEQUENCE: 230
tccgacaaat gggaac                                                    16
```

MAIZE PLANTS WITH IMPROVED DISEASE RESISTANCE

REFERENCE TO RELATED APPLICATION

This application claims the benefit of U.S. Provisional Application No. 62/331,918, filed May 4, 2016, which is herein incorporated by reference in its entirety.

INCORPORATION OF SEQUENCE LISTING

A sequence listing containing the file named "MONS390US_ST25.txt" which is 80,783 bytes (measured in MS-Windows®) and created on May 1, 2017, and comprises 230 sequences, and is incorporated herein by reference in its entirety.

FIELD OF THE INVENTION

The present invention relates to the field of plant breeding and more specifically to methods and compositions for producing corn plants exhibiting improved disease resistance.

BACKGROUND

Stalk rot infection reduces the efficiency of carbohydrate transport from the stalk up to the ears during grainfill, which reduces crop yield. A corn plant will die altogether if infection advances to the point that the pith pulls away from the outer rind of the stalk, which can eventually result in a stalk consisting of little more than a hollow tube that is no longer able transport water and nutrients to the rest of the plant. Furthermore, a stalk weakened by infection is more likely to collapse at one or more points along its length (lodging), which typically results in a plant that yields no harvestable grain. Stalk rots typically reduce yields up to 5% in almost any field where corn is cultivated. In years with particularly bad infection rates, yield losses reach 10-20%, and in some locations when infection is particularly acute, 100% yield loss can occur.

One of the most common forms of stalk rot is *Fusarium* stalk rot (FSR), caused by several species of fungi, including *Fusarium verticilliodes, Fusarium proliferatum*, and *Fusarium subglutinans*. FSR infection is characterized by rotting roots, crown, and lower internodes that begins shortly after pollination and progresses as the plant matures. Eventually the pith will disintegrate resulting in weak, spongy stalks that are prone to lodging.

Due to the lack of fungicides and or other chemical controls for FSR, growers are faced with limited options for managing the disease. Since the most effective approach is to select hybrids that are intrinsically resistant, what is needed are methods of identifying genetic sources of FSR resistance and more effective methods of introgressing those genetic elements into commercial lines to provide new hybrids with improved genetic resistance to FSR infection.

SUMMARY OF THE INVENTION

Identifying and selecting plants that exhibit resistance to *Fusarium* stalk rot (FSR) using marker-assisted selection (MAS) provides an effective and efficient method of improving the survivability of corn to FSR infection. This invention provides marker loci and quantitative trait loci (QTL) chromosome intervals that demonstrate significant co-segregation with FSR resistance. These markers, or additional loci linked to these markers, can be used in MAS breeding programs to produce plants with improved FSR resistance.

Marker loci and quantitative trait loci (QTL) chromosome intervals that demonstrate significant co-segregation with FSR resistance are provided. These markers, or additional loci linked to these markers, can be used in MAS breeding programs to produce plants with improved FSR resistance.

The FSR_2.01, FSR_5.01, FSR_6.01 and FSR_7.01 loci correspond to QTL discovered on chromosomes 2, 5, 6, and 7, respectively, of the corn genome. These loci contain genotypes closely linked to FSR resistance. Embodiments of this invention include methods of detecting genotypes within and/or linked to FSR_2.01, FSR_5.01, FSR_6.01 or FSR_7.01 to create disease resistant corn lines. Provided herein are examples of markers that are useful for detecting the presence or absence of disease resistance alleles linked to FSR_2.01, FSR_5.01, FSR_6.01 or FSR_7.01 as part of a MAS breeding program to produce plants with improved resistance to FSR infection.

Embodiments of this invention include identifying one or more corn plants with FSR resistance, improved resistance, or susceptibility to FSR infection by using a marker within the FSR_2.01, FSR_5.01, FSR_6.01 or FSR_7.01 chromosome intervals, or a marker closely linked to FSR_2.01, FSR_5.01, FSR_6.01 or FSR_7.01. As used herein, "closely linked" means that the marker or locus is within about 20 cM, preferably within about 15 cM, more preferably within about 10 cM, even more preferably within about 5 cM, even more preferably within about 1 cM, even more preferably about 0.5 cM, and even more preferably less than 0.5 cM of the identified FSR locus.

The location in the maize genome of FSR_2.01, FSR_5.01, FSR_6.01 and FSR_7.01, and chromosome intervals and sub-intervals containing markers closely linked to FSR_2.01, FSR_5.01, FSR_6.01 and FSR_7.01, are referenced herein to a public maize genome map (IBM2 2008 Neighbors). Genomic markers such as npi610 and gpm365a can be used to define the flanks of the FSR_2.01 chromosome interval, which includes markers closely linked to FSR_2.01. Genomic markers such as hmg2 and agrp90 can be used to define the flanks of the FSR_5.01 chromosome interval, which includes markers closely linked to FSR_5.01. Genomic markers such as gpm674c and TIDP5534 can be used to define the flanks of the FSR_6.01 chromosome interval, which includes markers closely linked to FSR_6.01. Genomic markers such as TIDP2919 and IDP5002 can be used to define the flanks of the FSR_7.01 chromosome interval, which includes markers closely linked to FSR_7.01. Other genomic markers may be used to define chromosome sub-intervals linked to FSR-FSR_2.01, FSR_5.01, FSR_6.01 or FSR_7.01.

Embodiments of this invention include methods of creating a population of corn plants with enhanced FSR resistance by providing a first population of corn plants, detecting the presence of a genetic marker that is genetically linked to FSR_2.01 by 20 cM or less in the first population, selecting one or more corn plants containing said marker from the first population of corn plants, and producing a population of offspring from at least one of said selected corn plants. In other embodiments, the genetic marker detected is genetically linked to FSR_2.01 by less than 15 cM, 10 cM, 5 cM, 1 cM, or 0.5 cM of FSR_2.01.

In another embodiment of this invention, a population of corn plants with enhanced FSR resistance is created by providing a first population of corn plants, detecting the presence of a genetic marker within the FSR_2.01 chromosome interval, selecting one or more corn plants containing said marker from the first population of corn plants, and producing a population of offspring from at least one of said selected corn plants. The FSR_2.01 chromosome interval includes any marker flanked by npi610 and gpm365a, including SEQ ID NOs: 1-3. Sub-intervals of the FSR_2.01 chromosome interval are also useful for this invention, and include any interval wherein one or both borders of the sub-interval are between npi610 and gpm365a. In one embodiment, an FSR_2.01 sub-interval is flanked by, and includes, SEQ ID NO: 1 and SEQ ID NO: 3. All manner of chromosome interval lengths between, and including, npi610 and gpm365a can be used in conjunction with this invention.

In another embodiment of this invention, a population of corn plants with enhanced FSR resistance is created by providing a first population of corn plants, detecting the presence of a genetic marker that is selected from the group consisting of SEQ ID NOs: 1-3 in the first population, selecting one or more corn plants containing said marker from the first population of corn plants, and producing a population of offspring from at least one of said selected corn plants.

Embodiments of this invention further include methods of creating a population of corn plants with enhanced FSR resistance by providing a first population of corn plants, detecting the presence of a genetic marker that is genetically linked to FSR_5.01 by 20 cM or less in the first population, selecting one or more corn plants containing said marker from the first population of corn plants, and producing a population of offspring from at least one of said selected corn plants. In other embodiments, the genetic marker detected is genetically linked to FSR_5.01 by less than 15 cM, 10 cM, 5 cM, 1 cM, or 0.5 cM of FSR_5.01.

In another embodiment of this invention, a population of corn plants with enhanced FSR resistance is created by providing a first population of corn plants, detecting the presence of a genetic marker within the FSR_5.01 chromosome interval, selecting one or more corn plants containing said marker from the first population of corn plants, and producing a population of offspring from at least one of said selected corn plants. The FSR_5.01 chromosome interval includes any marker flanked by hmg2 and agrp90, including SEQ ID NOs: 4-7. Sub-intervals of the FSR_5.01 chromosome interval are also useful for this invention, and include any interval wherein one or both borders of the sub-interval are between hmg2 and agrp90. In one embodiment, an FSR_5.01 sub-interval is flanked by, and includes, SEQ ID NO: 4 and SEQ ID NO: 7. All manner of chromosome interval lengths between, and including, hmg2 and agrp90 can be used in conjunction with this invention.

In another embodiment of this invention, a population of corn plants with enhanced FSR resistance is created by providing a first population of corn plants, detecting the presence of a genetic marker that is selected from the group consisting of SEQ ID NOs: 4-7 in the first population, selecting one or more corn plants containing said marker from the first population of corn plants, and producing a population of offspring from at least one of said selected corn plants.

Embodiments of this invention further include methods of creating a population of corn plants with enhanced FSR resistance by providing a first population of corn plants, detecting the presence of a genetic marker that is genetically linked to FSR_6.01 by 20 cM or less in the first population, selecting one or more corn plants containing said marker from the first population of corn plants, and producing a population of offspring from at least one of said selected corn plants. In other embodiments, the genetic marker detected is genetically linked to FSR_6.01 by less than 15 cM, 10 cM, 5 cM, 1 cM, or 0.5 cM of FSR_6.01.

In another embodiment of this invention, a population of corn plants with enhanced FSR resistance is created by providing a first population of corn plants, detecting the presence of a genetic marker within the FSR_6.01 chromosome interval, selecting one or more corn plants containing said marker from the first population of corn plants, and producing a population of offspring from at least one of said selected corn plants. The FSR_6.01 chromosome interval includes any marker flanked by gpm674c and TIDP5534, including SEQ ID NOs: 8-23. Sub-intervals of the FSR_6.01 chromosome interval are also useful for this invention, and include any interval wherein one or both borders of the sub-interval are between gpm674c and TIDP5534. In one embodiment, an FSR_6.01 sub-interval is flanked by, and includes, SEQ ID NO: 8 and SEQ ID NO: 23. All manner of chromosome interval lengths between, and including, gpm674c and TIDP5534 can be used in conjunction with this invention.

In another embodiment of this invention, a population of corn plants with enhanced FSR resistance is created by providing a first population of corn plants, detecting the presence of a genetic marker that is selected from the group consisting of SEQ ID NOs: 8-23 in the first population, selecting one or more corn plants containing said marker from the first population of corn plants, and producing a population of offspring from at least one of said selected corn plants.

Embodiments of this invention further include methods of creating a population of corn plants with enhanced FSR resistance by providing a first population of corn plants, detecting the presence of a genetic marker that is genetically linked to FSR_7.01 by 20 cM or less in the first population, selecting one or more corn plants containing said marker from the first population of corn plants, and producing a population of offspring from at least one of said selected corn plants. In other embodiments, the genetic marker detected is genetically linked to FSR_7.01 by less than 15 cM, 10 cM, 5 cM, 1 cM, or 0.5 cM of FSR_7.01.

In another embodiment of this invention, a population of corn plants with enhanced FSR resistance is created by providing a first population of corn plants, detecting the presence of a genetic marker within the FSR_7.01 chromosome interval, selecting one or more corn plants containing said marker from the first population of corn plants, and producing a population of offspring from at least one of said selected corn plants. The FSR_7.01 chromosome interval includes any marker flanked by TIDP2919 and IDP5002, including SEQ ID NOs: 24-27. Sub-intervals of the FSR_7.01 chromosome interval are also useful for this invention, and include any interval wherein one or both borders of the sub-interval are between TIDP2919 and IDP5002. In one embodiment, an FSR_7.01 sub-interval is flanked by, and includes, SEQ ID NO: 24 and SEQ ID NO: 27. All manner of chromosome interval lengths between, and including, TIDP2919 and IDP5002 can be used in conjunction with this invention.

In another embodiment of this invention, a population of corn plants with enhanced FSR resistance is created by providing a first population of corn plants, detecting the presence of a genetic marker that is selected from the group consisting of SEQ ID NOs: 24-27 in the first population, selecting one or more corn plants containing said marker from the first population of corn plants, and producing a population of offspring from at least one of said selected corn plants.

In one aspect, the present invention provides a method of obtaining a corn plant with enhanced *Fusarium* stalk rot resistance comprising: a) providing a population of corn plants; b) detecting in said plants the presence of a *Fusarium* stalk rot resistance allele at a polymorphic locus genetically linked to a chromosomal segment; and c) selecting from said population at least a first plant comprising said allele and enhanced *Fusarium* stalk rot resistance compared to a plant lacking said allele. In some embodiments, said segment is flanked by marker loci npi610 and gpm365a on chromosome 2, or flanked by marker loci hmg2 and agrp90 on chromosome 5, or flanked by marker loci gpm674c and TIDP5534 on chromosome 6, or flanked by marker loci TIDP2919 and IDP5002 on chromosome 7. In further embodiments, said segment is flanked by marker loci SEQ ID NO: 1 and SEQ ID NO: 3 on chromosome 2, or by marker loci SEQ ID NO: 4 and SEQ ID NO: 7 on chromosome 5, or by marker loci SEQ ID NO: 8 and SEQ ID NO: 23 on chromosome 6, for example by marker loci SEQ ID NO: 141 and SEQ ID NO: 143 on chromosome 6, or by marker loci SEQ ID NO: 24 and SEQ ID NO: 27 on chromosome 7. In other embodiments, said polymorphic locus comprises a nucleic acid sequence selected from the group consisting of SEQ ID NOs: 1-27 and 136-154. In some embodiments, said method further comprises selecting from said population at least two plants, thereby forming a population of corn plants comprising said allele and enhanced *Fusarium* stalk rot resistance compared to a plant lacking said allele. In certain embodiments, said *Fusarium* stalk rot resistance allele was introgressed into said population of corn plants from a starting plant or population of corn plants containing said allele. In other embodiments, said method further comprises producing a progeny plant with *Fusarium* stalk rot resistance from said first plant. In some embodiments, producing the progeny plant comprises marker-assisted selection for *Fusarium* stalk rot resistance. In further embodiments, said progeny plant is an F2-F6 progeny plant. In yet further embodiments, producing said progeny plant comprises backcrossing.

In another aspect, the invention provides a method of producing a corn plant with enhanced *Fusarium* stalk rot resistance comprising: a) crossing a first corn plant comprising a *Fusarium* stalk rot resistance allele with a second corn plant of a different genotype to produce one or more progeny plants; and b) selecting a progeny plant based on the presence of said allele at a polymorphic locus genetically linked to a chromosomal segment; wherein said allele confers enhanced resistance to *Fusarium* stalk rot compared to a plant lacking said allele. In some embodiments, said segment is flanked by marker loci npi610 and gpm365a on chromosome 2, or flanked by marker loci hmg2 and agrp90 on chromosome 5, or flanked by marker loci gpm674c and TIDP5534 on chromosome 6, or flanked by marker loci TIDP2919 and IDP5002 on chromosome 7. In further embodiments, said segment is flanked by marker loci SEQ ID NO: 1 and SEQ ID NO: 3 on chromosome 2, or by marker loci SEQ ID NO: 4 and SEQ ID NO: 7 on chromosome 5, or by marker loci SEQ ID NO: 8 and SEQ ID NO: 23 on chromosome 6, for example by marker loci SEQ ID NO: 141 and SEQ ID NO: 143 on chromosome 6, or by marker loci SEQ ID NO: 24 and SEQ ID NO: 27 on chromosome 7. In some embodiments, said polymorphic locus comprises a nucleic acid sequence selected from the group consisting of SEQ ID NO: 1-27 and 136-154. In certain embodiments, said progeny plant is an F2-F6 progeny plant. In other embodiments, producing said progeny plant comprises backcrossing. In some embodiments, backcrossing comprises from 2-7 generations of backcrosses. In further embodiments, backcrossing comprises marker-assisted selection in at least two generations. In yet further embodiments, backcrossing comprises marker-assisted selection in all generations. In some embodiments, said first corn plant is an inbred or a hybrid. In other embodiments, said second corn plant is an agronomically elite corn plant. In further embodiments, said agronomically elite corn plant is an inbred or a hybrid.

DETAILED DESCRIPTION OF THE INVENTION

I. Chromosome Intervals

The term "chromosome interval" designates a contiguous linear span of genomic DNA that resides in planta on a single chromosome. The term also designates any and all genomic intervals defined by any of the markers set forth in this invention. The genetic elements located on a single chromosome interval are physically linked and the size of a chromosome interval is not particularly limited. In some aspects, the genetic elements located within a single chromosome interval are genetically linked, typically with a genetic recombination distance of, for example, less than or equal to 20 cM, or alternatively, less than or equal to 10 cM. That is, two genetic elements within a single chromosome interval undergo meiotic recombination at a frequency of less than or equal to 20% or 10%, respectively.

The boundaries of a chromosome interval can be defined by genetic recombination distance or by markers. In one embodiment, the boundaries of a chromosome interval comprise markers. In another embodiment, the boundaries of a chromosome interval comprise markers that will be linked to the gene controlling the trait of interest, i.e., any marker that lies within a given interval, including the terminal markers that defining the boundaries of the interval, and that can be used as a marker for the presents or absence of disease resistance. In one embodiment, the intervals described herein encompass marker clusters that co-segregate with disease resistance. The clustering of markers occurs in relatively small domains on the chromosomes, indicating the presence of a genetic locus controlling the trait of interest in those chromosome regions. The interval encompasses markers that map within the interval as well as the markers that define the terminal.

An interval described by the terminal markers that define the endpoints of the interval will include the terminal markers and any marker localizing within that chromosome domain, whether those markers are currently known or unknown. Although it is anticipated that one skilled in the art may describe additional polymorphic sites at marker loci in and around the markers identified herein, any marker within the chromosome intervals described herein that are associated with disease resistance fall within the scope of this claimed invention.

"Quantitative trait loci" or a "quantitative trait locus" (QTL) is a genetic domain that effects a phenotype that can be described in quantitative terms and can be assigned a "phenotypic value" which corresponds to a quantitative value for the phenotypic trait. A QTL can act through a single gene mechanism or by a polygenic mechanism. In some aspects, the invention provides QTL chromosome intervals, where a QTL (or multiple QTLs) that segregates with disease resistance is contained in those intervals. In one embodiment of this invention, the boundaries of chromosome intervals are drawn to encompass markers that will be linked to one or more QTL. In other words, the chromosome interval is drawn such that any marker that lies within that interval (including the terminal markers that define the boundaries of the interval) is genetically linked to the QTL. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention. FSR_2.01, FSR_5.01, FSR_6.01, and FSR_7.01 Chromosome Intervals In one embodiment, the present invention provides a plant comprising a nucleic acid molecule selected from the group consisting of SEQ ID NO: 1-27 and 136-154, fragments thereof, and complements of both. In another embodiment, the present invention also provides a plant comprising the alleles of the FSR_2.01, FSR_5.01, FSR_6.01, or FSR_7.01 chromosome intervals, or fragments and complements thereof, as well as any plant comprising any combination of one or more disease resistance loci linked to at least one marker selected from the group consisting of SEQ ID NOs: 1-27 and 136-154. Such alleles may be homozygous or heterozygous.

The locations in the maize genome of FSR_2.01, FSR_5.01, FSR_6.01, or FSR_7.01 and the chromosome intervals comprising markers closely linked to it are disclosed in Table 6. Genetic map loci are represented in cM, with position zero being the first (most distal) marker known at the beginning of the chromosome on both Monsanto's internal consensus genetic map and the Neighbors 2008 maize genomic map, which is freely available to the public from the Maize GDB website and commonly used by those skilled in the art.

For example, the FSR_2.01 chromosome interval comprises SEQ ID NOs: 1-3 and is flanked by the markers npi610 and gpm365a. This chromosome interval encompasses a marker cluster that co-segregates with FSR resistance in the populations studied at a p-value <0.001.

Similarly, the FSR_5.01 chromosome interval contains SEQ ID NOs: 4-7 and is flanked by the markers hmg2 and agrp90. This chromosome interval encompasses a marker cluster that co-segregates with FSR resistance in the populations studied at a p-value <0.001.

The FSR_6.01 chromosome interval contains SEQ ID NOs: 8-23 and 136-154 and is flanked by the markers gpm674c and TIDP5534. This chromosome interval encompasses a marker cluster that co-segregates with FSR resistance in the populations studied at a p-value <0.001. The FSR_6.01 interval provided herein comprises a chromosomal interval flanked by marker loci SEQ ID NOs: 141 and SEQ ID NO: 143 and comprising marker locus SEQ ID NO: 142.

The FSR_7.01 chromosome interval contains SEQ ID NOs: 24-27 and is flanked by the markers TIDP2919 and IDP5002. This chromosome interval encompasses a marker cluster that co-segregates with FSR resistance in the populations studied at a p-value <0.001.

Thus, one skilled in the art can use this invention to improve the efficiency of breeding for improved disease resistance in maize by associating disease resistance phenotypes with genotypes at previously unknown disease resistance loci in the maize genome. Disclosed herein are chromosome intervals that comprise alleles responsible for phenotypic differences between disease resistant and disease susceptible corn lines. Each chromosome interval is characterized by the genomic regions flanked by and including the markers npi610 and gpm365a on chromosome 2; or hmg2 and agrp90 on chromosome 5; or gpm674c and TIDP5534 on chromosome 6; or TIDP2919 and IDP5002 on chromosome 7, and comprise markers within or closely linked to (within 20 cM of) FSR_2.01, FSR_5.01, FSR_6.01, or FSR_7.01, respectively. The invention also comprises other intervals genetically linked with those intervals.

Examples of markers useful for this purpose comprise the SNP markers listed in Table 6, or any marker that maps within the chromosome intervals described herein (including the termini of the intervals), or any marker linked to those markers. Such markers can be assayed simultaneously or sequentially in a single sample or population of samples.

Accordingly, the markers and methods of the present invention can be utilized to guide MAS or breeding maize varieties with the desired complement (set) of allelic forms of chromosome intervals associated with superior agronomic performance (resistance, along with any other available markers for yield, disease resistance, etc.). Any of the disclosed marker alleles can be introduced into a corn line via introgression, by traditional breeding (or introduced via transformation, or both) to yield a corn plant with superior agronomic performance. The number of alleles associated with resistance that can be introduced or be present in a corn plant of the present invention ranges from one to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein could be useful and within the scope of this invention.

Similarly, by identifying plants lacking the desired marker locus, susceptible or less resistant plants can be identified, and, e.g., eliminated from subsequent crosses. Similarly, these marker loci can be introgressed into any desired genomic background, germplasm, plant, line, variety, etc., as part of an overall MAS breeding program designed to enhance yield. The invention also provides chromosome QTL intervals that find equal use in MAS to select plants that demonstrate disease resistance or improved tolerance. Similarly, the QTL intervals can also be used to counter-select plants that are susceptible or have reduced resistance to disease.

The present invention also comprises methods of making a progeny corn plant and the progeny corn plants produced by these methods. The methods comprise crossing a first parent corn plant with a second corn plant and growing the female corn plant under plant growth conditions to yield corn plant progeny. Methods of crossing and growing corn plants are well within the ability of those of ordinary skill in the art. Such corn plant progeny can be assayed for alleles associated with resistance and, thereby, the desired progeny selected. Such progeny plants or seed can be sold commercially for corn production, used for food, processed to obtain a desired constituent of the corn, or further utilized in subsequent rounds of breeding. At least one of the first or second corn plants is a corn plant of the present invention in that it comprises at least one of the allelic forms of the markers of the present invention, such that the progeny are capable of inheriting the allele.

Often, a method of the present invention is applied to at least one related corn plant such as from progenitor or descendant lines in the subject corn plants' pedigree such that inheritance of the desired resistance allele can be traced. The number of generations separating the corn plants being subject to the methods of the present invention will generally be from 1 to 20, commonly 1 to 5, and typically 1, 2, or 3 generations of separation, and quite often a direct descendant or parent of the corn plant will be subject to the method (i.e., one generation of separation).

Thus, with this invention, one skilled in the art can detect the presence or absence of disease resistance genotypes in the genomes of corn plants as part of a marker assisted selection program. In one embodiment, a breeder ascertains the genotype at one or more markers for a disease resistant parent, which contains a disease resistance allele, and the genotype at one or more markers for a susceptible parent, which lacks the resistance allele. For example, the markers of the present invention can be used in MAS in crosses involving elite×exotic corn lines by subjecting the segregating progeny to MAS to maintain disease resistance alleles, or alleles associated with yield under disease conditions. A breeder can then reliably track the inheritance of the resistance alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the disease resistant parent can be reliably predicted to express the resistant phenotype; progeny that share genotypes with the disease susceptible parent can be reliably predicted to express the susceptible phenotype. Thus, the laborious and inefficient process of manually phenotyping the progeny for disease resistance is avoided.

By providing the positions in the maize genome of the intervals and the disease resistance associated markers within, this invention also allows one skilled in the art to identify other markers within the intervals disclosed herein or linked to the chromosome intervals disclosed herein.

Closely linked markers flanking the locus of interest that have alleles in linkage disequilibrium with a resistance allele at that locus may be effectively used to select for progeny plants with enhanced resistance to disease conditions. Thus, the markers described herein, such as those listed in Tables 1a or 1b, as well as other markers genetically or physically mapped to the same chromosome interval, may be used to select for maize plants with enhanced resistance to disease conditions. Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. In an introgression program, this allows for selection of the gene or locus genotype at the more proximal polymorphic markers and selection for the recurrent parent genotype at the more distal polymorphic markers.

The choice of markers actually used to practice this invention is not particularly limited and can be any marker that maps within the FSR_2.01, FSR_5.01, FSR_6.01, or FSR_7.01 chromosome intervals described herein, any marker closely linked (within 10 cM) to a marker in the FSR_2.01, FSR_5.01, FSR_6.01, or FSR_7.01 chromosome intervals, or any marker selected from SEQ ID NO: 1-27 and 136-154, or the markers listed in Table 6. Furthermore, since there are many different types of marker detection assays known in the art, it is not intended that the type of marker detection assay (e.g. RAPDs, RFLPs, SNPs, AFLPs, etc.) used to practice this invention be limited in any way.

II. Molecular Genetic Markers

"Marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A favorable allele of a marker is the allele of the marker that co-segregates with a desired phenotype (e.g., disease resistance). As used herein, a QTL marker has a minimum of one favorable allele, although it is possible that the marker might have two or more favorable alleles found in the population. Any favorable allele of that marker can be used advantageously for the identification and construction of disease resistant plant lines. Optionally, one, two, three or more favorable allele(s) of different markers are identified in, or introgressed into a plant, and can be selected for or against during MAS. Desirably, plants or germplasm are identified that have at least one such favorable allele that positively correlates with disease resistance or improved disease resistance. Alternatively, a marker allele that co-segregates with disease susceptibility also finds use with the invention, since that allele can be used to identify and counter select disease susceptible plants. Such an allele can be used for exclusionary purposes during breeding to identify alleles that negatively correlate with resistance, to eliminate susceptible plants or germplasm from subsequent rounds of breeding.

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of anyone particular marker) on the basis of polynucleotide length and/or sequence. A large number of corn molecular markers are known in the art, and are published or available from various sources, such as the MaizeGDB Internet resource. In general, any differentially inherited polymorphic trait (including a nucleic acid polymorphism) that segregates among progeny is a potential genetic marker.

In some embodiments of the invention, one or more marker alleles are selected for in a single plant or a population of plants. In these methods, plants are selected that contain favorable alleles from more than one resistance marker, or alternatively, favorable alleles from more than one resistance marker are introgressed into a desired germplasm. One of skill recognizes that the identification of favorable marker alleles is germplasm-specific. The determination of which marker alleles correlate with resistance (or susceptibility) is determined for the particular germplasm under study. One of skill recognizes that methods for identifying the favorable alleles are known in the art. Identification and use of such favorable alleles is within the scope of this invention. Furthermore still, identification of favorable marker alleles in plant populations other than the populations used or described herein is within the scope of this invention.

Marker Detection

In some aspects, methods of the invention utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is a SNP type marker, and the detected allele is a SNP allele, and the method of detection is allele specific hybridization (ASH).

In general, the majority of genetic markers rely on one or more property of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

While the exemplary markers provided in the figures and tables herein are either SNP markers, any of the aforementioned marker types can be employed in the context of the invention to identify chromosome intervals encompassing genetic element that contribute to superior agronomic performance (e.g., disease resistance or improved disease tolerance).

Probes and Primers

In general, synthetic methods for making oligonucleotides, including probes, primers, molecular beacons, PNAs, LNAs (locked nucleic acids), etc., are known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon. It is not intended that the nucleic acid probes of the invention be limited to any particular size.

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present invention.

III. Linkage Analysis and QTL

Linkage Analysis

"Linkage", or "genetic linkage," is used to describe the degree with which one marker locus is "associated with" another marker locus or some other locus (for example, a resistance locus). For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ is attributed to linkage. As used herein, linkage can be between two markers, or alternatively between a marker and a phenotype. A marker locus can be associated with (linked to) a trait, e.g., a marker locus can be associated with resistance or improved tolerance to a plant pathogen when the marker locus is in linkage disequilibrium (LD) with the resistance trait. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1. The phrase "closely linked," in the present application, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 20, 19, 18, 17, 16, 15, 14, 13, 12, 11, 10, 9, 8, 7, 6, 5, 4, 3, 2, 1, 0.75, 0.5 or 0.25 cM or less from each other.

Classical linkage analysis can be thought of as a statistical description of the relative frequencies of co segregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate. This can be expressed as a percentage of cosegregation (recombination frequency) or, also commonly, in centiMorgans (cM).

Linkage analysis is used to determine which polymorphic marker allele demonstrates a statistical likelihood of co-segregation with the resistance phenotype (thus, a "resistance marker allele"). Following identification of a marker allele for co-segregation with the resistance phenotype, it is possible to use this marker for rapid, accurate screening of plant lines for the resistance allele without the need to grow the plants through their life cycle and await phenotypic evaluations, and furthermore, permits genetic selection for the particular resistance allele even when the molecular identity of the actual resistance QTL is unknown. Tissue samples can be taken, for example, from the endosperm, embryo, or mature/developing plant and screened with the appropriate molecular marker to rapidly determine determined which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

Quantitative Trait Loci

An allele of a QTL can comprise multiple genes or other genetic factors even within a contiguous genomic region or linkage group, such as a haplotype. As used herein, an allele of a disease resistance locus can encompass more than one gene or nucleotide sequence where each individual gene or nucleotide sequence is also capable of exhibiting allelic variation and where each gene or nucleotide sequence is also capable of eliciting a phenotypic effect on the quantitative trait in question. In an aspect of the present invention the allele of a QTL comprises one or more genes or nucleic acid sequences that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular disease locus or for a particular polymorphic marker.

The principles of QTL analysis and statistical methods for calculating linkage between markers and useful QTL, or between any loci in a genome are well known in the art. Exemplary methods include penalized regression analysis, ridge regression, single point marker analysis, complex pedigree analysis, Bayesian MCMC, identity-by-descent analysis, interval mapping, composite interval mapping, and Haseman-Elston regression. QTL analyses are often performed with the help of a computer and specialized software available from a variety of public and commercial sources known to those of skill in the art.

IV. Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM). In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through Marker assisted selection (MAS), a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with the disease resistance phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

Association Mapping

Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable maize genetic map (for example, a composite map) can be used to help observe distribution of the identified QTL markers and/or QTL marker clustering using previously determined map locations of the markers.

V. Marker Assisted Selection, Plant Breeding, and Genomic Introgression Marker Assisted Selection "Introgression" refers to the transmission of a desired allele of a genetic locus from one genetic background to another by. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that are resistant, exhibit improved resistance or are susceptible to FSR infection by identifying plants having a specified allele that is linked to FSR_2.01, FSR_5.01, FSR_6.01, or FSR_7.01.

In general, MAS uses polymorphic markers that have been identified as having a significant likelihood of co-segregation with a resistance trait. Such markers are presumed to map near a gene or genes that give the plant its resistance phenotype, and are considered indicators for the desired trait, and are termed QTL markers. Plants are tested for the presence or absence of a desired allele in the QTL marker.

Identification of plants or germplasm that include a marker locus or marker loci linked to a resistance trait or traits provides a basis for performing marker assisted selection. Plants that comprise favorable markers or favorable alleles are selected for, while plants that comprise markers or alleles that are negatively correlated with resistance can be selected against. Desired markers and/or alleles can be introgressed into plants having a desired (e.g., elite or exotic) genetic background to produce an introgressed resistant plant or germplasm. In some aspects, it is contemplated that a plurality of resistance markers are sequentially or simultaneous selected and/or introgressed. The combinations of resistance markers that are selected for in a single plant is not limited, and can include any combination of markers disclosed herein or any marker linked to the markers disclosed herein, or any markers located within the QTL intervals defined herein.

In some embodiments, the allele that is detected is a favorable allele that positively correlates with disease resistance or improved disease tolerance. In the case where more than one marker is selected, an allele is selected for each of the markers; thus, two or more alleles are selected. In some embodiments, it can be the case that a marker locus will have more than one advantageous allele, and in that case, either allele can be selected. It will be appreciated that the ability to identify QTL marker loci alleles that correlate with resistance, improved tolerance, or susceptibility of a corn plant to disease conditions provides a method for selecting plants that have favorable marker loci as well. That is, any plant that is identified as comprising a desired marker locus (e.g., a marker allele that positively correlates with resistance) can be selected for, while plants that lack the locus, or that have a locus that negatively correlates with resistance, can be selected against.

In some embodiments, a disease resistant first corn plant or germplasm (the donor) can be crossed with a second corn plant or germplasm (the recipient, e.g., an elite or exotic corn, depending on characteristics that are desired in the progeny) to create an introgressed corn plant or germplasm as part of a breeding program designed to improve disease resistance of the recipient corn plant or germplasm. In some aspects, the recipient plant can also contain one or more disease resistant loci, which can be qualitative or quantitative trait loci. In another aspect, the recipient plant can contain a transgene.

In some embodiments, the recipient corn plant or germplasm will typically display reduced resistance to disease conditions as compared to the first corn plant or germplasm, while the introgressed corn plant or germplasm will display an increased resistance to disease conditions as compared to the second plant or germplasm. An introgressed corn plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one or multiple traits, e.g., multiple loci involved in resistance, or multiple loci each involved in resistance or tolerance to different diseases, the efficiency of MAS compared to phenotypic screening becomes even greater, because all of the loci can be evaluated in the lab together from a single sample of DNA.

Marker Assisted Backcrossing

One application of MAS is to use the resistance or improved tolerance markers to increase the efficiency of an introgression effort aimed at introducing a resistance QTL into a desired (typically high yielding) background. If the nucleic acids from a plant are positive for a desired genetic marker allele, the plant can be self-fertilized to create a true breeding line with the same genotype, or it can be crossed with a plant with the same marker or with other characteristics to create a sexually crossed hybrid generation.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable resistance marker loci) into an otherwise desirable genetic background from the recurrent parent (e.g., an otherwise high yielding line). The more cycles of back crossing that are done, the greater the genetic contribution of the recurrent parent to the resulting introgressed variety. This is often necessary, because resistant plants may be otherwise undesirable, e.g., due to low yield, low fecundity, or the like. In contrast, strains which are the result of intensive breeding programs may have excellent yield, fecundity or the like, merely being deficient in one desired trait such as resistance to FSR infection.

Moreover, in another aspect, while maintaining the introduced markers associated with resistance, the genetic contribution of the plant providing disease resistance can be reduced by back-crossing or other suitable approaches. In one aspect, the nuclear genetic material derived from the donor material in the plant can be less than or about 50%, less than or about 25%, less than or about 13%, less than or about 5%, 3%, 2% or 1%, but that the recipient remains resistant to disease.

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

Genomic Selection

Genomic selection (GS), also known as genome wide selection (GWS), is a form of MAS that estimates all locus, haplotype, and/or marker effects across the entire genome to calculate genomic estimated breeding values (GEBVs). See Nakaya and Isobe, Annals of Botany 110: 1303-1316 (2012); Van Vleck, et al., Journal of Animal Science 70: 363-371 (1992); and Heffner, et al., Crop Science 49: 1-12 (2009). GS utilizes a training phase and a breeding phase. In the training phase, genotypes and phenotypes are analyzed in a subset of a population to generate a GS prediction model that incorporates significant relationships between phenotypes and genotypes. A GS training population must be representative of selection candidates in the breeding program to which GS will be applied. In the breeding phase, genotype data are obtained in a breeding population, then favorable individuals are selected based on GEBVs obtained using the GS prediction model generated during the training phase without the need for phenotypic data.

Larger training populations typically increase the accuracy of GEBV predictions. Increasing the training population to breeding population ratio is helpful for obtaining accurate GEBVs when working with populations having high genetic diversity, small breeding populations, low heritability of traits, or large numbers of QTLs. The number of markers required for GS modeling is determined based on the rate of LD decay across the genome, which must be calculated for each specific population to which GS will be applied. In general, more markers will be necessary with faster raters of LD decay. Ideally, GS comprises at least one marker in LD with each QTL, but in practical terms one of ordinary skill in the art would recognize that this is not necessary.

With genotyping data, favorable individuals from a population can be selected based only on GEBVs. GEBVs are the sum of the estimate of genetic deviation and the weighted sum of estimates of breed effects, which are predicted using phenotypic data. Without being limiting, commonly used statistical models for prediction of GEBVs include best linear unbiased prediction (Henderson, *Biometrics* 31: 423 (1975)) and a Bayesian framework (Gianola and Fernando, *Journal of Animal Science* 63: 217-244 (1986)).

The compositions and methods of the present disclosure can be utilized for GS or breeding corn varieties with a desired complement (set) of allelic forms of chromosome intervals associated with superior agronomic performance (e.g., FSR resistance). In an aspect, a corn plant or seed provided herein can be selected using genomic selection. In another aspect, SEQ ID NOs: 1-27 and 136-154 can be used in a method comprising genomic selection. In another aspect, a genomic selection method provided herein comprises phenotyping a population of corn plants for FSR resistance using the FSR infection rating scale provided in Table 1. In another aspect, a genomic selection method provided herein comprises genotyping a population of corn plants or seeds with at least one of marker loci SEQ ID NOs: 1-27 and 136-154.

VI. Transgenic Plants
Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the present disclosure, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant.

Regulatory elements such as promoters, leaders, enhancers, introns, and transcription termination regions (or 3' UTRs) can play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron. In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, that splicing per se is not required, as IME in dicotyledonous plants has been shown by point mutations within the splice sites of the pat1 gene from *A. thaliana*. Multiple uses of the same intron in one plant have been shown to exhibit disadvantages. In those cases, it is necessary to have a collection of basic control elements for the construction of appropriate recombinant DNA elements.

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Regulatory elements may be characterized by their gene expression pattern, e.g., positive and/or negative effects, such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. As used herein, the term "chimeric" refers to a single DNA molecule produced by fusing a first DNA molecule to a second DNA molecule, where neither the first nor the second DNA molecule would normally be contained in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the disclosure.

In specific embodiments, chimeric DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

Exemplary promoters for expression of a nucleic acid sequence include plant promoters such as the CaMV 35S promoter, or others such as CaMV 19S, nos, Adh, sucrose synthase, α-tubulin, actin, cab, PEPCase or those promoters associated with the R gene complex. Tissue-specific promoters such as leaf specific promoters, or tissue selective promoters (e.g., promoters that direct greater expression in leaf primordia than in other tissues), and tissue-specific enhancers are also contemplated to be useful, as are inducible promoters such as ABA- and turgor-inducible promoters. Any suitable promoters known in the art may be used to express defensin or defensin-like coding sequences in a plant. In an embodiment, the CaMV35S promoter may be used to express defensin or defensin-like coding sequences in a plant. In yet another embodiment, a disease or pathogen inducible promoter can be used to express defensin or defensin like proteins. Examples of disease or pathogen inducible promoters can be found in Kooshki et al. Plant Science 165 (2003) 213-219, Koschmann et al. Plant Physiology 160 (2012) 178-191, Rushton et al. The Plant Cell, 14 (2002) 749-762, and Kirsch et al. The Plant Journal (2001) 26 217-227.

The DNA sequence between the transcription initiation site and the start of the coding sequence, i.e., the untranslated leader sequence, can also influence gene expression. As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. One may thus wish to employ a particular leader sequence with a transformation construct of the present disclosure. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of defensin or defensin-like coding sequences.

Transformation constructs prepared in accordance with the present disclosure may further include a 3' end DNA sequence that acts as a signal to terminate transcription and allow for the polyadenylation of the mRNA produced by coding sequences operably linked to a promoter. As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR. In one embodiment, the native terminator of a defensin or defensin-like coding sequence may be used. Alternatively, a heterologous 3' end may enhance the expression of sense or antisense defensin or defensin-like coding sequences.

Sequences that are joined to the coding sequence of an expressed gene, which are removed post-translationally from the initial translation product and which facilitate the transport of the protein into or through intracellular or extracellular membranes, are termed transit or targeting peptide (usually into vacuoles, vesicles, plastids and other intracellular organelles) and signal peptide or sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein.

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the present disclosure.

Selectable marker transgenes may also be used with the present disclosure. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the present disclosure are known in the art and include, but are not limited to, transcribable DNA molecules encoding β-glucuronidase (GUS), green fluorescent protein (GFP), proteins that confer antibiotic resistance, and proteins that confer herbicide tolerance.

VII. Plant Cell Transformation Methods

Numerous methods for transforming chromosomes in a plant cell with recombinant DNA are known in the art and are used in methods of producing a transgenic plant cell and plant. Two effective methods for such transformation are Agrobacterium-mediated transformation and microprojectile bombardment-mediated transformation. Microprojectile bombardment methods are illustrated in U.S. Pat. Nos. U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). Agrobacterium-mediated transformation methods are described in U.S. Pat. Nos. U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), and US Patent Application Publication Nos. US 2004/0087030 A1 (cotton), and US 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having another recombinant DNA that confers another trait, for example herbicide resistance or pest resistance or enhanced water use efficiency, to produce progeny plants having recombinant DNA that confers both traits. Typically, in such breeding for combining traits the transgenic plant donating the additional trait is the male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant DNA, by application using a selective agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

VIII. Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits, such as resistance to *Fusarium* stalk rot in maize Seed Treatment In an aspect, a method, a corn plant, or a corn seed provided herein is used in combination with one or more pesticides including, but not limited to, herbicides, fungicides (e.g., picoxystrobin, cyproconazole, tetraconazole, pyraclostrobin, metconazole, azoxystrobin, propiconazole, prothioconazole, trifloxystrobin), insecticides, microbiocides, nematicides, insect repellents, bactericides, and other substances used to control pests. In another aspect, a method, a corn plant, or a corn seed provided herein is used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which can be applied as a seed treatment, a foliar treatment, a drench treatment, or a drip treatment.

In an aspect, corn seeds provided herein are untreated. In another aspect, corn seeds provided herein can be subjected to various and multiple treatments. For example, without being limiting, the seeds can be treated to improve germination by priming the seeds, by disinfection to protect against seed borne pathogens, or both priming and disinfection. In another example, seeds can be coated with any available coating to improve, for example, plantability, seed emergence, and protection against seed borne pathogens. Seed coating can be any form of seed coating including, but not limited to, pelleting, film coating, and encrustments.

IX. General Terms and Definitions

Systems, including automated systems for selecting plants that comprise a marker of interest and/or for correlating presence of the marker with resistance are also a feature of the invention. These systems can include probes relevant to marker locus detection, detectors for detecting labels on the probes, appropriate fluid handling elements and temperature controllers that mix probes and templates and/or amplify templates and systems instructions that correlate label detection to the presence of a particular marker locus or allele.

In an aspect, this invention could be used on any plant. In another aspect, the plant is selected from the genus *Zea*. In another aspect, the plant is selected from the species *Zea mays*. In a further aspect, the plant is selected from the subspecies *Zea mays* L. ssp. mays. In an additional aspect, the plant is selected from the group *Zea mays* L. subsp. mays Indentata, otherwise known as dent corn. In another aspect, the plant is selected from the group *Zea mays* L. subsp. mays Indurata, otherwise known as flint corn. In an aspect, the plant is selected from the group *Zea mays* L. subsp. mays *Saccharata*, otherwise known as sweet corn. In another aspect, the plant is selected from the group *Zea mays* L. subsp. mays Amylacea, otherwise known as flour corn. In a further aspect, the plant is selected from the group *Zea mays* L. subsp. mays Everta, otherwise known as pop corn. *Zea* plants include hybrids, inbreds, partial inbreds, or members of defined or undefined populations.

In a preferred aspect, the present invention provides a plant to be assayed for resistance or susceptibility to disease by any method to determine whether a plant is resistant, susceptible, or whether it exhibits some degree of resistance or susceptibility. Populations of plants can be similarly characterized in this manner, or further characterized as segregating for the trait of disease resistance.

It is further understood that a plant of the present invention may exhibit the characteristics of any relative maturity group. In an aspect, the maturity group is selected from the group consisting of early maturing varieties, mid-season maturing varieties, and full season varieties.

The present invention also provides for parts of the plants of the present invention. Plant parts, without limitation, include seed, endosperm, ovule and pollen. In a particularly preferred aspect of the present invention, the plant part is a seed.

In another aspect, the corn seed can be subjected to various treatments. For example, the seeds can be treated to improve germination by priming the seeds or by disinfection to protect against seed-borne pathogens. In another aspect, seeds can be coated with any available coating to improve, for example, plantability, seed emergence, and protection against seed-borne pathogens. Seed coating can be any form of seed coating including, but not limited to, pelleting, film coating, and encrustments.

In another aspect, the corn plant can show a comparative resistance compared to a non-resistant control corn plant. In this aspect, a control corn plant will preferably be genetically similar except for the disease resistance allele or alleles in question. Such plants can be grown under similar conditions with equivalent or near equivalent exposure to the pathogen.

Various patent and non-patent publications are cited herein, the disclosures of each of which are incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

Descriptions of commonly used breeding terms and methods for crossing and producing hybrids that are used to describe present invention can be found in one of several reference books (Allard, "Principles of Plant Breeding,"

John Wiley & Sons, N.Y., U. of CA, Davis, Calif., 50-98, 1960; Simmonds, "Principles of crop improvement," Longman, Inc., N.Y., 369-399, 1979; Sneep and Hendriksen, "Plant breeding perspectives," Wageningen (ed), *Center for Agricultural Publishing and Documentation,* 1979; Fehr, In: Soybeans: Improvement, Production and Uses, 2nd Edition, Monograph., 16:249, 1987; Fehr, "Principles of variety development," Theory and Technique, (Vol. 1) and Crop Species Soybean (Vol. 2), Iowa State Univ., Macmillan Pub. Co., N.Y., 360-376, 1987).

The definitions and methods provided define the present invention and guide those of ordinary skill in the art in the practice of the present invention. Unless otherwise noted, terms are to be understood according to conventional usage by those of ordinary skill in the relevant art. Examples of resources describing many of the terms related to molecular biology used herein can be found in in Alberts et al., Molecular Biology of The Cell, $5^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes Icorn, Oxford University Press: New York, 2007. The nomenclature for DNA bases as set forth at 37 CFR § 1.822 is used.

Definitions

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Adjacent", when used to describe a nucleic acid molecule that hybridizes to DNA containing a polymorphism, refers to a nucleic acid that hybridizes to DNA sequences that directly about the polymorphic nucleotide base position. For example, a nucleic acid molecule that can be used in a single base extension assay is "adjacent" to the polymorphism.

"Allele" generally refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease prone plants. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, seeds or plants) and includes crosses between plants (sexual) and self-fertilization (selfing).

"Elite line" means any line that has resulted from breeding and selection for superior agronomic performance. Numerous elite lines are available and known to those of skill in the art of corn breeding. An "elite population" is an assortment of elite individuals or lines that can be used to represent the state of the art in terms of agronomically superior genotypes of a given crop species, such as corn. Similarly, an "elite germplasm" or elite strain of germplasm is an agronomically superior germplasm, typically derived from and/or capable of giving rise to a plant with superior agronomic performance, such as an existing or newly developed elite line of corn. In contrast, an "exotic line" or "exotic germplasm" is a line or germplasm derived from a plant not belonging to an available elite line or strain of germplasm. In the context of a cross between two plants or lines of germplasm, an exotic germplasm is not closely related by descent to the elite germplasm with which it is crossed. Most commonly, the exotic germplasm is not derived from any known elite line of a crop, but rather is selected to introduce genetic elements (typically desired alleles) into a breeding program.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

"Genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of several genes.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

"Linkage disequilibrium" or "LD" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The tern "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

"Locus" a chromosome region where a polymorphic nucleic acid, trait determinant, gene or marker is located. The loci of this invention comprise one or more polymorphisms in a population; i.e., alternative alleles are present in some individuals. A "gene locus" is a specific chromosome location in the genome of a species where a specific gene can be found.

"Marker Assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc. "Marker Assisted Selection" (MAS) is a process by which phenotypes are selected based on marker genotypes.

"Molecular phenotype" is a phenotype detectable at the level of a population of one or more molecules. Such molecules can be nucleic acids, proteins, or metabolites. A molecular phenotype could be an expression profile for one or more gene products, e.g., at a specific stage of plant development, in response to an environmental condition or stress, etc.

"Operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Percent identity" or "% identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence.

"Phenotype" means the detectable characteristics of a cell or organism which can be influenced by genotype.

"Plant" refers to a whole plant any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a resistance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

"Resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different corn line) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant lines, or plant families under disease conditions, and furthermore, will also recognize the phenotypic gradations of "resistant."

"Resistance locus" means a locus that contributes resistance, tolerance, or susceptibility to *Fusarium* stalk rot.

"Resistance allele" means the nucleic acid sequence associated with resistance or tolerance to disease.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Tolerance" or "improved tolerance" in a plant to disease conditions is an indication that the plant is less affected by disease conditions with respect to yield, survivability and/or other relevant agronomic measures, compared to a less resistant, more "susceptible" plant. Tolerance is a relative term, indicating that a "tolerant" plant survives and/or produces better yields in disease conditions compared to a different (less tolerant) plant (e.g., a different corn line strain) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance or susceptibility of different plants, plant lines or plant families under disease conditions, and furthermore, will also recognize the phenotypic gradations of "tolerant."

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Vector" is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "sub cloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

"Yield" is the culmination of all agronomic traits as determined by the productivity per unit area of a particular plant product of commercial value. "Agronomic traits," include the underlying genetic elements of a given plant variety that contribute to yield over the course of growing season.

X. Deposit Information

A deposit of at least 625 F1 hybrid seeds resulting from the cross of corn lines CV353184 and CV056579 has been made with the Provasoli-Guillard National Center for Marine Algae and Microbiota (NCMA), 60 Bigelow Drive, East Boothbay, Me., 04544 USA. The seeds are deposited under NCMA Accession No. 202009006. The date of the deposit is Sep. 24, 2020. Access to the deposit will be available during the pendency of the application to persons entitled thereto upon request. The deposit has been accepted under the Budapest Treaty and will be maintained in the NCMA Depository, which is a public depository, for a period of 30 years, or 5 years after the most recent request, or for the enforceable life of the patent, whichever is longer, and will be replaced if nonviable during that period. Applicant does not waive any infringement of their rights granted

EXAMPLES

Example 1. Identification of FSR QTLs

Corn plants were inoculated 10 days after flowering by injecting an internode of each stalk with $2\times10^5$ *Fusarium moniliforme* spores suspended in 2 mL of distilled water. Six weeks after inoculation, the severity of *Fusarium* stalk rot in each plant was visually assessed by splitting stalks longitudinally to expose the pith. Internodes at the site of inoculation were examined to determine the percent of the internode showing visual lesions characteristic of the disease (necrosis), as summarized in Table 1. The individual plant scores of each row were then averaged to generate a final score for the row.

TABLE 1

Rating scale of relative FSR infection resistance phenotypes.

| % Internode Necrosis | Score | Rating |
|---|---|---|
| 0-10% | 1 | Highly resistant |
| 10-20% | 2 | Highly resistant |
| 20-30% | 3 | Resistant |
| 30-40% | 4 | Resistant |
| 40-50% | 5 | Intermediate |
| 50-60% | 6 | Susceptible |
| 60-70% | 7 | Susceptible |
| >80% | 8 | Highly susceptible |
| >80% and necrosis expands to adjacent internode | 9 | Highly susceptible |

Parental lines were selected from Monsanto proprietary inbred lines as shown in Table 2.

TABLE 2

Bi-parental mapping populations.

| Mapping Population | Cross | Resistant Line | Susceptible Line | Population Type | Population Size |
|---|---|---|---|---|---|
| A | CV119351/CV120707 | CV119351 | CV120707 | Double-haploid | 192 |
| B | CV122159/CV119964 | CV119964 | CV122159 | F3 | 204 |
| C | CV335662*2/CV353184 | CV353184 | CV335662 | BC1F4 | 192 |
| D | CV123496/CV124239 | CV123496 | CV124239 | Double-haploid | 208 |
| E | CV355838/CV123302 | CV355838 | CV123302 | Double-haploid | 108 |

Plants from all mapping populations were then genotyped using SNP markers that collectively spanned each chromosome in the maize genome. The primer sequences for amplifying exemplary SNP marker loci linked to the FSR and the probes used to genotype the corresponding SNP sequences are provided in Table 3. One of skill in the art will recognize that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Configuration of the amplification primers and detection probes can also be varied. Thus, the invention is not limited to the primers, probes, or marker sequences specifically recited herein.

TABLE 3

Exemplary SNP markers associated with FSR resistance.

| | | SEQ ID NO. | | | |
|---|---|---|---|---|---|
| SEQ ID NO. | SNP Position | Fwd Primer | Rev Primer | Probe 1 | Probe 2 |
| 1 | 351 | 28 | 55 | 82 | 109 |
| 2 | 338 | 29 | 56 | 83 | 110 |
| 3 | 341 | 30 | 57 | 84 | 111 |
| 4 | 329 | 31 | 58 | 85 | 112 |
| 5 | 275 | 32 | 59 | 86 | 113 |
| 6 | 323 | 33 | 60 | 87 | 114 |
| 7 | 918 | 34 | 61 | 88 | 115 |
| 8 | 262 | 35 | 62 | 89 | 116 |
| 9 | 118 | 36 | 63 | 90 | 117 |
| 10 | 115 | 37 | 64 | 91 | 118 |
| 11 | 209 | 38 | 65 | 92 | 119 |
| 12 | 262 | 39 | 66 | 93 | 120 |
| 13 | 101 | 40 | 67 | 94 | 121 |
| 14 | 82 | 41 | 68 | 95 | 122 |
| 15 | 618 | 42 | 69 | 96 | 123 |
| 16 | 101 | 43 | 70 | 97 | 124 |
| 17 | 117 | 44 | 71 | 98 | 125 |
| 18 | 101 | 45 | 72 | 99 | 126 |
| 19 | 101 | 46 | 73 | 100 | 127 |
| 20 | 279 | 47 | 74 | 101 | 128 |
| 21 | 462 | 48 | 75 | 102 | 129 |
| 22 | 27 | 49 | 76 | 103 | 130 |
| 23 | 148 | 50 | 77 | 104 | 131 |
| 24 | 204 | 51 | 78 | 105 | 132 |
| 25 | 342 | 52 | 79 | 106 | 133 |
| 26 | 133 | 53 | 80 | 107 | 134 |
| 27 | 456 | 54 | 81 | 108 | 135 |

In an illustrative example, SNP marker SEQ ID NO: 1 can be amplified using the primers described in Table 3 as SEQ ID NO: 28 (forward primer) and SEQ ID NO: 55 (reverse primer), and detected with probes indicated as SEQ ID NO: 82 (Probe 1) and SEQ ID NO: 109 (Probe 2). Marker-trait association studies were performed using both single-marker analysis (SMA) and composite interval mapping (CIM). For each marker, the thresholds of likelihood ratio between full and null models for CIM were based on 1000 random permutation tests and the thresholds (p-value) for SMA were based on 10,000 random permutation tests (Churchill and Doerg, 1994). The composite interval mapping (CIM) analysis revealed several strong QTLs associated with FSR resistance. Genetic map loci are represented in cM, with position zero being the first (most distal) marker known at the beginning of the chromosome on Monsanto's internal consensus genetic map. Each row of Table 4 provides mapping population ID, number of SNP markers genotyped, resistant parent, chromosome position, the peak of the Likelihood ratio corresponding to FSR resistance, QTL interval where left and right flanking positions are shown, p-value, additive effect, and the phenotypic variance ($R^2$) of individual QTL.

TABLE 4

CIM results from all mapping populations.

| Mapping Population | #Mk | Resistant Parent | Chr | QTL Positions (cM) | | | p-value | Additive | QTL R² |
|---|---|---|---|---|---|---|---|---|---|
| | | | | Peak | Left Flank | Right Flank | | | |
| A | 292 | CV119351 | 2 | 175.6 | 173.6 | 186.1 | 0.01 | 0.76 | 0.149 |
| B | 128 | CV119964 | 5 | 144.8 | 138.2 | 154.8 | 0.01 | 0.82 | 0.18 |
| C | 169 | CV353184 | 6 | 54.7 | 44.5 | 62.7 | 0.01 | 0.69 | 0.28 |
| D | 137 | CV123496 | 6 | 56.9 | 48.9 | 67.8 | 0.01 | 0.48 | 0.18 |
| E | 149 | CV355838 | 7 | 60.3 | 47.3 | 64.5 | 0.01 | 0.55 | 0.18 |

*p-value is based on 1,000 permutation tests

The identified QTLs were designated as FSR_2.01, FSR_5.01, FSR_6.01 and FSR_7.01 (Table 5).

TABLE 5

Summary of FSR QTLs

| Chromosome | QTL interval (cM) | IBM2008 Map (IcM) | Flanking Markers | | QTL Designation |
|---|---|---|---|---|---|
| | | | Left | Right | |
| 2 | 173-187 | 568-607 | npi610 | gpm365a | FSR_2.01 |
| 5 | 138-155 | 483-524 | hmg2 | agrp90 | FSR_5.01 |
| 6 | 44-68 | 216-318 | gpm674c | TIDP5534 | FSR_6.01 |
| 7 | 47-65 | 99-248 | TIDP2919 | IDP5002 | FSR_7.01 | cM = centiMorgans;
IcM = map units of the IBM2 2008 Neighbors Genetic Map;
flanking markers available on the publically available IBM2 2008 Neighbors Genetic Map In Table 5, "IcM" refers to the map units of the IBM2 2008 Neighbors Genetic Map, which was generated with an intermated recombinant inbred population (syn 4) that resulted in approximately a four-fold increase in the number of meioses as compared to the typical recombination experiment that is used to generate centiMorgan (cM) distances (Lee, et al., 2002, *Plant Mol Biol* 48:453 and the Maize Genetics and Genomics Database). "cM" refers to the classical definition of a centimorgan wherein one cM is equal to a 1% chance that a trait at one genetic locus will be separated from a trait at another locus due to crossing over in a single generation (meaning the traits cosegregate 99% of the time during meiosis), and this definition is used herein to delineate map locations pertaining to this invention.

Table 6 lists the effect estimates on FSR rating score for each marker (SEQ ID NO.) linked to FSR resistance based on SMA. Each row of Table 6 provides the SEQ ID NO. of the marker, chromosome position, marker position on Monsanto's internal consensus genetic map and the Neighbors 2008 maize genomic map (publicly available on the internet; Andorf, et al. (2015) MaizeGDB 2015: New tools, data, and interface for the maize model organism database. *Nucleic Acids Research*), genetic source of resistant allele, resistant allele, susceptible allele, the estimated effect that the marker polymorphism had on the FSR rating score and p-value based on permutation test. For example, SEQ ID NO: 14 was associated with a reduction of 0.51 in FSR rating score by one copy of the resistant allele. However, one of skill in the art will recognize that a "resistant" allele at one locus may be a "susceptible" allele in a different genetic background. Thus, the invention is not limited to the "resistant" and "susceptible" alleles exemplified herein.

TABLE 6

Estimate effects of markers linked to FSR resistance from all mapping populations by SMA.

| SEQ ID NO. | Chromosome | MON Map cM | IBM2008 Map IcM | Genetic Source of Resistant Allele | Resistant allele | Susceptible allele | Single Allele Effect | Permutation Testing Probability |
|---|---|---|---|---|---|---|---|---|
| 1 | 2 | 170.6 | 558.6 | CV119351 | C | T | 0.255 | 0.001 |
| 2 | 2 | 176.9 | 582.4 | CV119351 | C | T | 0.568 | 0.001 |
| 3 | 2 | 186.1 | 603.2 | CV119351 | A | C | 0.405 | 0.001 |
| 4 | 5 | 129.7 | 453.9 | CV119964 | C | G | 0.473 | 0.001 |
| 5 | 5 | 132.8 | 465.5 | CV119964 | A | G | 0.512 | 0.001 |
| 6 | 5 | 148.8 | 508.5 | CV119964 | G | A | 0.703 | 0.001 |
| 7 | 5 | 157.7 | 532.5 | CV119964 | G | A | 0.566 | 0.001 |
| 8 | 6 | 38.6 | 201.1 | CV353184 | A | G | 0.445 | 0.001 |
| 9 | 6 | 50.7 | 234.3 | CV353184 | T | C | 0.601 | 0.001 |
| 10 | 6 | 59.4 | 267.1 | CV353184 | G | A | 0.586 | 0.001 |
| 11 | 6 | 68.3 | 318.7 | CV353184 | G | C | 0.445 | 0.001 |
| 12 | 6 | 38.6 | 201.1 | CV123496 | G | A | 0.364 | 0.001 |

TABLE 6-continued

Estimate effects of markers linked to FSR resistance from all mapping populations by SMA.

| SEQ ID NO. | Chromosome | MON Map cM | IBM2008 Map IcM | Genetic Source of Resistant Allele | Resistant allele | Susceptible allele | Single Allele Effect | Permutation Testing Probability |
|---|---|---|---|---|---|---|---|---|
| 13 | 6 | 48.9 | 229.4 | CV123496 | A | G | 0.421 | 0.001 |
| 14 | 6 | 52.7 | 0.0 | CV123496 | C | T | 0.51 | 0.001 |
| 15 | 6 | 58.6 | 262.3 | CV123496 | G | C | 0.447 | 0.001 |
| 16 | 6 | 62.6 | 295.7 | CV123496 | C | T | 0.422 | 0.001 |
| 17 | 6 | 63.6 | 300.8 | CV123496 | T | C | 0.376 | 0.001 |
| 18 | 6 | 64.1 | 302.7 | CV123496 | C | T | 0.441 | 0.001 |
| 19 | 6 | 64.5 | 304.1 | CV123496 | G | T | 0.384 | 0.001 |
| 20 | 6 | 66.0 | 312.3 | CV123496 | A | G | 0.379 | 0.001 |
| 21 | 6 | 66.3 | 313.2 | CV123496 | C | T | 0.36 | 0.001 |
| 22 | 6 | 67.4 | 316.2 | CV123496 | G | A | 0.361 | 0.001 |
| 23 | 6 | 69.0 | 320.7 | CV123496 | A | G | 0.388 | 0.001 |
| 24 | 7 | 45.3 | 95.5 | CV355838 | G | C | 0.484 | 0.001 |
| 25 | 7 | 51.8 | 118.5 | CV355838 | C | T | 0.426 | 0.001 |
| 26 | 7 | 59.3 | 152.1 | CV355838 | G | A | 0.432 | 0.001 |
| 27 | 7 | 65.7 | 248.0 | CV355838 | A | T | 0.522 | 0.001 |

*p-value is based on 10,000 permutation tests

Example 2. Validation of FSR QTLs

Plants with or without resistant FSR QTL were derived. Plants carrying the resistant allele of FSR-2.01 or FSR-6.01 showed significant reductions in FSR rating score when compared to plants carrying the susceptible allele (Table 7).

TABLE 7

Validation of FSR QTLs

| QTL interval | Resistance QTL Profile | FSR Infection Score | StdErr | p-value |
|---|---|---|---|---|
| FSR_2.01 | Absent | 2.97 | 0.16 | 2.22E−02 |
|  | Present | 2.6 | 0.17 |  |
| FSR_6.01 | Absent | 3.5 | 0.1 | 2.05E−07 |
|  | Present | 2.8 | 0.1 |  |

Present: with resistant QTL
Absent: without resistant QTL

Example 3. Fine-Mapping of FSR Resistance QTL on Chromosome 6

In order to obtain additional recombinants, CV353184/CV056579 derived F1 lines were selected, self-crossed, and harvested. CV353184 is a FSR resistant line. CV056579 is a FSR susceptible line and is disclosed in U.S. Patent Publication No. 2016/0270355, published on Sep. 22, 2016, the entire content of which is incorporated by reference herein. The resulting segregating F2 kernels were chipped and genotyped with 23 SNP markers within 46.9-64.2 cM on chromosome 6 based on the internal consensus genetic map (Table 8).

TABLE 8

Primers and probes used for detecting SNPs linked to FSR-6.01 in the fine-mapping

| | | SEQ ID NO. | | | |
|---|---|---|---|---|---|
| SEQ ID NO. | SNP Position | Fwd Primer | Rev Primer | Probe 1 | Probe 2 |
| 136 | 101 | 155 | 174 | 193 | 212 |
| 13 | 101 | 40 | 67 | 94 | 121 |
| 137 | 101 | 156 | 175 | 194 | 213 |
| 138 | 162 | 157 | 176 | 195 | 214 |
| 9 | 118 | 36 | 63 | 90 | 117 |
| 139 | 101 | 158 | 177 | 196 | 215 |
| 140 | 74 | 159 | 178 | 197 | 216 |
| 141 | 130 | 160 | 179 | 198 | 217 |
| 142 | 409 | 161 | 180 | 199 | 218 |
| 143 | 101 | 162 | 181 | 200 | 219 |
| 144 | 101 | 163 | 182 | 201 | 220 |
| 145 | 101 | 164 | 183 | 202 | 221 |
| 10 | 115 | 37 | 64 | 91 | 118 |
| 146 | 101 | 165 | 184 | 203 | 222 |
| 147 | 102 | 166 | 185 | 204 | 223 |
| 148 | 101 | 167 | 186 | 205 | 224 |
| 16 | 101 | 43 | 70 | 97 | 124 |
| 149 | 179 | 168 | 187 | 206 | 225 |
| 150 | 747 | 169 | 188 | 207 | 226 |
| 151 | 101 | 170 | 189 | 208 | 227 |
| 152 | 101 | 171 | 190 | 209 | 228 |
| 153 | 101 | 172 | 191 | 210 | 229 |
| 154 | 101 | 173 | 192 | 211 | 230 |

Kernels were bulked based on their haplotypes within this QTL region. These bulks (10-20 plants/bulk) were then planted and subsequently screened for FSR resistance via progeny test at three locations. In Table 9, grey cells with bold and underlined font indicated that the bulk carried the same alleles as the susceptible inbred line at the specific SNP position. White cells Cells without bold or underlined font indicated that the bulk carried the same allele as the resistant inbred line at the specific SNP position. For example, bulk "k" shared the same candidate QTL region as the susceptible inbred line, CV056579. The individual plant scores of each bulk were averaged. The average was reported as a final score for the bulk and then compared with that of susceptible line. Bulk "d", "e" and "f" displayed significantly reduced FSR severity (highlighted by black box, p-value <0.05).

Based on the common SNP (highlighted by black oval) of these bulks, SEQ ID NO: 142 was identified as the peak SNP marker. The two closest SNP markers flanking SEQ ID NO: 142 are SEQ ID NO: 141 and SEQ ID NO: 143.

TABLE 9

Fine-mapping of FSR-6.01 from CV353184/CV056579

| SEQ ID | 136 | 13 | 137 | 138 | 9 | 139 | 140 | 141 | 142 | 143 | 144 | 145 | 10 | 146 | 147 | 148 | 16 | 149 | 150 | 151 | 152 | 153 | 154 | LSMean | StdDev |
|---|---|---|---|---|---|---|---|---|---|---|---|---|---|---|---|---|---|---|---|---|---|---|---|---|---|
| MON v5.2 pos(cM) | 46.9 | 48.9 | 49.6 | 49.7 | 50.7 | 51.5 | 53.9 | 53.9 | 54.1 | 56.8 | 57.6 | 58.6 | 59.4 | 61.5 | 61.8 | 61.9 | 62.6 | 62.7 | 62.7 | 63.2 | 63.9 | 64.2 | 64.2 | | |
| CV056579 | GG | GG | GG | GG | CC | CC | TT | GG | CC | TT | GG | AA | AA | GG | GG | AA | CC | TT | TT | TT | AA | AA | CC | 6.38 | 0.1 |
| CV353184 | AA | AA | AA | CC | TT | AA | CC | AA | AA | CC | AA | CC | GG | AA | GG | GG | TT | CC | CC | AA | GG | CC | TT | 2.8 | 0.57 |
| a | AA | GG | GG | GG | TT | CC | TT | GG | AA | TT | GG | AA | AA | GG | GG | AA | CC | TT | TT | TT | AA | AA | CC | 7.46 | 0.71 |
| b | AA | AA | AA | CC | TT | AA | TT | GG | AA | TT | GG | AA | GG | GG | GG | AA | CC | TT | TT | TT | AA | AA | CC | 7.2 | 0.65 |
| c | AA | GG | GG | GG | TT | AA | CC | AA | AA | TT | GG | AA | AA | GG | GG | AA | CC | TT | TT | TT | AA | AA | CC | 7.07 | 0.91 |
| d | AA | AA | AA | CC | TT | AA | CC | AA | AA | CC | AA | AA | AA | GG | GG | AA | CC | TT | TT | TT | AA | AA | CC | 5.38 | 0.73 |
| e | GG | GG | GG | GG | TT | AA | CC | AA | AA | CC | AA | CC | GG | AA | AA | GG | TT | CC | CC | AA | GG | CC | TT | 4.83 | 0.77 |
| f | GG | GG | GG | GG | CC | CC | TT | GG | AA | CC | AA | CC | GG | AA | AA | GG | TT | CC | CC | AA | GG | CC | TT | 5.22 | 0.99 |
| g | GG | GG | GG | GG | CC | CC | TT | GG | CC | TT | GG | AA | AA | GG | GG | AA | TT | TT | TT | AA | GG | CC | TT | 6.78 | 0.88 |
| h | GG | GG | GG | GG | CC | CC | TT | GG | CC | TT | GG | AA | GG | GG | GG | AA | TT | CC | CC | AA | GG | CC | TT | 6.38 | 0.47 |
| i | GG | GG | GG | GG | CC | CC | TT | GG | CC | TT | GG | AA | AA | GG | GG | AA | TT | CC | CC | AA | GG | CC | TT | 6.97 | 1.1 |
| j | GG | GG | GG | GG | CC | CC | TT | GG | CC | TT | GG | AA | GG | GG | GG | AA | CC | TT | TT | TT | AA | AA | CC | 6.68 | 0.1 |
| k | GG | GG | GG | GG | CC | CC | TT | GG | CC | TT | GG | AA | AA | GG | GG | AA | CC | TT | TT | TT | AA | AA | CC | 6.7 | 0.1 |

For example, bulk "a" shared the same alleles as the resistant inbred line (CV353184) at the SNP positions represented by SEQ ID NO: 136 and SEQ ID NO: 13 (highlighted by white cells without bold or underlined font). Bulk "a" shared the same alleles as the susceptible inbred line (CV056579) at the rest of SNP positions (highlighted by grey cells with bold and underlined font).

The QTL region associated with FSR resistance was fine-mapped to 53.9-56.8 cM on chromosome 6 based on the internally-derived genetic map (Table 10).

TABLE 10

Summary of fine-mapping result

| SEQ ID NO. | MON Map cM | Marker Profile | IBM2008 Map IcM |
| --- | --- | --- | --- |
| 141 | 53.9 | Left flanking marker | 242.7 |
| 142 | 54.1 | QTL peak | 243.2 |
| 143 | 56.8 | Right flanking marker | 255.2 |

What is claimed is:

1. A method of obtaining a corn plant with enhanced *Fusarium* stalk rot resistance comprising:
   a) providing a population of corn plants;
   b) detecting in said plants the presence of a *Fusarium* stalk rot resistance allele at a polymorphic locus genetically linked to a chromosomal segment flanked by marker loci SEQ ID NO: 141 and SEQ ID NO: 143 on chromosome 6, wherein representative seed comprising said allele have been deposited under NCMA Accession No. 202009006;
   c) selecting from said population at least a first plant based on the presence of said *Fusarium* stalk rot resistance allele and exhibiting enhanced *Fusarium* stalk rot resistance when compared to a plant lacking said allele; and
   d) assaying said plant comprising said *Fusarium* stalk rot resistance allele for resistance to *Fusarium verticilliodes, Fusarium proliferatum*, or *Fusarium subglutinans*.

2. The method of claim 1, wherein said polymorphic locus comprises a nucleic acid sequence selected from the group consisting of SEQ ID NOs:141-143.

3. The method of claim 1, further defined as comprising selecting from said population at least two plants, thereby forming a population of corn plants comprising said allele and enhanced *Fusarium* stalk rot resistance compared to a plant lacking said allele.

4. The method of claim 1, wherein said *Fusarium* stalk rot resistance allele was introgressed into said population of corn plants from a starting plant or population of corn plants containing said allele.

5. The method of claim 1, further comprising producing a progeny plant with *Fusarium* stalk rot resistance from said first plant.

6. The method of claim 5, wherein producing the progeny plant comprises marker-assisted selection for *Fusarium* stalk rot resistance.

7. The method of claim 5, wherein the progeny plant is an F2-F6 progeny plant.

8. The method of claim 5, wherein producing the progeny plant comprises backcrossing.

9. A method of producing a corn plant with enhanced *Fusarium* stalk rot resistance comprising:
   a) crossing a first corn plant comprising a *Fusarium* stalk rot resistance allele with a second corn plant of a different genotype to produce one or more progeny plants;
   b) selecting a progeny plant based on the presence of said allele at a polymorphic locus genetically linked to a chromosomal segment flanked by marker loci SEQ ID NO: 141 and SEQ ID NO: 143 on chromosome 6, wherein said allele confers enhanced resistance to *Fusarium* stalk rot compared to a plant lacking said allele, and wherein representative seed comprising said allele have been deposited under NCMA Accession No. 202009006; and
   c) assaying said progeny plant comprising said allele for resistance to *Fusarium verticilliodes, Fusarium proliferatum*, or *Fusarium subglutinans*.

10. The method of claim 9, wherein said polymorphic locus comprises a nucleic acid sequence selected from the group consisting of SEQ ID NOs: 141-143.

11. The method of claim 9, wherein the progeny plant is an F2-F6 progeny plant.

12. The method of claim 9, wherein producing the progeny plant comprises backcrossing.

13. The method of claim 12, wherein backcrossing comprises from 2-7 generations of backcrosses.

14. The method of claim 12, wherein backcrossing comprises marker-assisted selection in at least two generations.

15. The method of claim 14, wherein backcrossing comprises marker-assisted selection in all generations.

16. The method of claim 9, wherein the first corn plant is an inbred or a hybrid.

17. The method of claim 9, wherein the second corn plant is an agronomically elite corn plant.

18. The method of claim 17, wherein the agronomically elite corn plant is an inbred or a hybrid.

\* \* \* \* \*